(12) United States Patent
Taylor et al.

(10) Patent No.: US 7,141,373 B2
(45) Date of Patent: Nov. 28, 2006

(54) METHOD OF HAPLOTYPE-BASED GENETIC ANALYSIS FOR DETERMINING RISK FOR DEVELOPING INSULIN RESISTANCE AND CORONARY ARTERY DISEASE

(75) Inventors: Kent D. Taylor, Ventura, CA (US); Jerome I. Rotter, Los Angeles, CA (US); Huiying Yang, Cerritos, CA (US); Willa A. Hsueh, Pacific Palisades, CA (US); Xiuqing Guo, Santa Monica, CA (US); Leslie J. Raffel, Los Angeles, CA (US); Mark O. Goodarzi, Los Angeles, CA (US)

(73) Assignees: Cedars-Sinai Medical Center, Los Angeles, CA (US); The Regents of the University of California, Oakland, CA (US)

(*) Notice: Subject to any disclaimer, the term of this patent is extended or adjusted under 35 U.S.C. 154(b) by 529 days.

(21) Appl. No.: 10/463,301

(22) Filed: Jun. 16, 2003

(65) Prior Publication Data

US 2004/0076988 A1   Apr. 22, 2004

Related U.S. Application Data

(60) Provisional application No. 60/388,726, filed on Jun. 14, 2002.

(51) Int. Cl.
C12Q 1/68 (2006.01)
C12P 19/34 (2006.01)
C07H 21/04 (2006.01)

(52) U.S. Cl. .................. 435/6; 435/91.2; 536/23.2; 536/23.5

(58) Field of Classification Search .................. None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,988,617 | A | 1/1991 | Landegren et al. |
| 5,384,242 | A | 1/1995 | Oakes |
| 6,297,014 | B1 | 10/2001 | Taylor et al. |

OTHER PUBLICATIONS

Anderson et al (1999) Journal of the American Collge of Cardiology, 'Association of lipoprotein lipase gene polymorphisms with coronary artery disease', vol. 33, No. 4, pp. 1013-1020.*
Ballantyne, C. M., Low-density lipoproteins and risk for coronary artery disease, *Am. J. Cardiol.*, 82(9A):3Q-12Q (Nov. 5, 1998).
Campeau, Lucien et al., The Relation of Risk Factors to the Development of Atherosclerosis in Saphenous-vein Bypass Grafts and the Progression of Disease in the Native Circulation, *The New England Journal of Medicine*, vol. 311, No. 21, pp. 1329-1332 (Nov. 22, 1984).
Campeau, Lucien et al., The Effect of Aggressive Lowering of Low-Density Lipoprotein Cholesterol Levels and Low-Dose Anticoagulation on Obstructive Changes in Saphenous-vein Coronary-Artery Bypass Grafts, *The New England Journal of Medicine*, vol. 336, No. 3, pp. 153-162 (Jan 16, 1997).
Chen, L. et al., HindIII DNA polymorphism in the lipoprotein lipase gene and plasma lipid phenotypes and carotid artery atherosclerosis, *Hum Genet*, 98(5):551-556 (Nov. 1996).
Chuat, J. C. et al., The lipoprotein lipase-encoding human gene: sequence from intron-6 to intron-9 and presence in intron-7 of a 40-million-year-old Alu sequence, *Gene*, 110(2):257-61 (Jan. 15, 1992).
Clark, A. G. Et al., Haplotype structure and population genetic inferences from nucleotide-sequence variation in human lipoprotein lipase, *Am J. Hum Genet*, 63(2):595-612 (Aug. 1998).
Deeb, Samir S., et al., Structure of the Human Lipoprotein Lipase Gene, *Biochemistry*, vol. 28, No. 10, pp. 4131-4135 (May 16, 1989).
Fisher, R. M. et al., Common variation in the lipoprotein lipase gene: effects on plasma lipids and risk of atherosclerosis, *Atherosclerosis*, 135(2):145-59 (Dec. 1997). Abstract Only.
Funke Harald et al., The low down on lipoprotein lipase, *Nature Genetics*, vol. 10, pp. 6-7 (May 1995).
Gerdes, C. et al., Polymorphisms in the lipoprotein lipase gene and their associations with plasma lipid concentrations in 40-year-old Danish men, *Circulation*, 92(7):1765-1769 (Oct. 1995).
Hayden, M. R. et al., Molecular genetics of human lipoprotein lipase deficiency, *Mol Cell Biochem*, 113(2):171-176 (Aug. 18, 1992).
Kirchgessner, T. G. et al., Organization of the human lipoprotein lipase gene and evolution of the lipase gene family, *Proc Natl Acad Sci USA*, vol. 86, No. 24, pp. 9647-9651 (Dec. 1989).
Kleyn, Patrick W. et al., Genetic Variation as a Guide to Drug Development, *Science*, vol. 281, pp. 1820-1821 (Sep. 18, 1998).
Kornitzer, M., Primary and secondary prevention of coronary artery disease: a follow-up on clinical controlled trials, *Curr Opin Lipidol*, 9(6):557-64 (Dec. 1998). Abstract Only.
Kozaki, K. et al., Mutational analysis of human lipoprotein lipase by carboxy-terminal truncation, *J Lipid Res*, 34(10):1765-1772 (Oct. 1993). Abstract Only.
Mori, A. et al., Development of a direct DNA sequencing method for detecting heterozygous mutations of the human lipoprotein lipase gene, *Clin Biochem*, 30(4):315-324, (Jun. 1997). Abstract Only.

(Continued)

*Primary Examiner*—Diana Johannsen
*Assistant Examiner*—Stephen Kapushoc
(74) *Attorney, Agent, or Firm*—Perkins Coie LLP

(57) ABSTRACT

Disclosed is a method for determining haplotypes useful for large-scale genetic analysis, within a genomic reference sequence of interest, for a human subpopulation. The method can applied to statistically evaluating the genotypes of subjects for any statistically significant association with a phenotype of interest, such as insulin resistance or coronary artery disease. Thus, also disclosed are a method of detecting a genetic predisposition in a Mexican-American human subject for developing insulin resistance and methods of detecting a lower than normal risk in a Mexican-American human subject for developing insulin resistance or coronary artery disease.

3 Claims, 3 Drawing Sheets

OTHER PUBLICATIONS

Neitzel, Gary F. et al., Atheroscleoris in Aortocoronary Bypass Grafts, Morphologic Study and Risk Factor Analysis 6 to 12 Years After Surgery, *Arteriosclerosis*, vol. 6.No. 6, pp. 594-600 (Nov./Dec. 1986).

Nickerson, Deborah A. et al., DNA sequence diversity in a 9.7-kb region of the human lipoprotein lipase gene, *Nature Genetics*, vol. 19, No. 3, pp. 233-240 (Jul. 1998).

Oka, Kazuhiro et al., Structure and polymorphic map of human lipoprotein lipase gene, Biohimica et Biophysica Acta, vol. 1049, pp. 21-26 (1990).

Peacock, Rachel E. et al., Associaions between lipoprotein lipase gene polymorphisms and plasma correlations of lipids, lipoproteins and lipase activities in young myocardial infraction survivors and age-matched healthy individuals from Sweden, *Arthersclerosis*, Vo. 97, pp. 171-185 (1992).

Reymer, P. W. et al., A lipoprotein lipase mutation (Asn291Ser) is associated with reduced HDL cholesterol levels in premature atherosclerosis, *Nat Genet*, 10(1):28-34 (May 1995).

Rifkind, B. M., Clinical trials of reducing low-density lipoprotein concentrations, *Endocrinol Metab Clin North Am*, 27(3):585-95, viii-ix (Sep. 1998). Abstract Only.

Sass, C. et al., Evidence for a cholesterol-lowering gene in a French-Canadian kindred with familial hypercholesterolemia, *Hum Genet*, 96(1):21-26 (Jul. 1995).

Wion, Karen L. et al., Human Lipoprotein Lipase complementary DNA Sequence, *Science*, vol. 235, pp. 1638-1641 (Mar. 27, 1987).

Zuliani, Giovanni et al., Tetranucleotide repeat polymorphism in the LPL gene, Nucleic Acids Res., vol. 18, No. 16, p. 4958 (1990).

Kuivenhoven, Jan Albert et al., The role of a Common Variant of the Cholesteryl Ester Transfer Protein Gee in the Progression of Coronary Atherosclerosis, *The New England Journal of Medicine*, vol. 338, No. 2, pp. 86-93 (Jan. 8, 1998).

Santamarina-Fojo, Silvia et al., Structure, function and role of lipoprotein lipase in lipoprotein metabolism, *Genetics and Molecular Biology, Current Opinion in Lipidology*, vol. 5, pp. 117-125 (1994).

Abecasis GR, Cookson WO, Cardon LR. Pedigree tests of transmission disequilibrium. Eur J Hum Genet 2000;8:545-51.

Abecasis GR, Cardon LR, Cookson WO. A general test of association for quantitative traits in nuclear families. Am J Hum Genet 2000;66:279-92.

Ahn, Y.I. et al., Two DNA polymorphisms in the lipoprotrein lipase gene and their associations with factors related to cariovascular disease, *J Lipid Res*, 34:421-8 (Mar. 1993).

Ahn, Y.I., Ferrell, R.E., Hamman, R.F., and Kamboh, M.I. (1993) Association of lipoprotein lipase gene variation with the physiological components of the insulin-resistance syndrome in the population of the San Luis Valley, Colorado. Diabetes Care, 16 (11), 1502-1506.

Allayee H, de Bruin TW, Michelle Dominguez K, et al. Genome scan for blood pressure in Dutch dyslipidemic families reveals linkage to a locus on chromosome 4p. Hyptertension 2001;38:773-8.

Allison DB. Transmission-disequilibrium tests for quantitative traits. Am J Hum Genet 1997;60:676-90.

Chamberlain, J.C. et al., DNA polymorphisms at the lipoprotein lipase gene: associations in normal and hypertriglyceridaemic subjects, *Atherosclerosis*, 79(1):85-91 (Sep. 1989).

Cole SA, Aston CE, Hamman RF, Ferrell RE. Association of a Pvull RFLP at the lipoprotein lipase locus with fasting insulin levels in Hispanic men. Genet Epidemiol 1993;10:177-88.

Daly MJ, Rioux JD, Schaffner SF, Hudson TJ, Lander ES. High-resolution haplotype structure in the human genome. Nat Genet 2001;29:229-232.

DeFronzo RA, Tobin JD, Andres R. Glucose clamp technique: a method for quantifying insulin secretion and resistance. Am J Physiol 1979;237:E214-23.

Despres JP, Lamarche B, Mauriege P, et al. Hyperinsulinemia as an independent risk factor for ischemic heart disease. N Engl J Med 1996;334(15):952-7.

Eisenberg S. High density lipoprotein metabolism. J Lipid Res 1984; 25:1017-58.

Elston RC, Buxbaum S, Jacobs KB, Olson JM. Haseman and Elston revisited. Genet Epidemiol 2000;19:1-17.

Freeman MS, Mansfield MW, Barrett JH, Grant PJ. Heritability of features of the insulin resistance syndrome in a community-based study of healthy families. Diabet Med 2002;19:994-9.

Gabriel SB, Schaffner SF, Nguyen H, Moore JM, Roy J, Blumenstiel B, Higgins J, DeFelice M, Lochner A, Faggart M, Liu-Cordero SN, Rotimi C, Adeyemo A, Cooper R, Ward R, Lander ES, Daly MJ, Altshuler D. The structure of haplotype blocks in the human genome. Science 2002;296:2225-2229.

Gaziano JM, Hennekens CH, O'Donnell CJ, Breslow JL, Buring JE. Fasting triglycerides, high-density lipoprotein, and risk of myocardial infarction. Circulation 1997;96:2520-5.

Georges, J. L. et al., Family study of lipoprotein lipase gene polymorphisms and plasma triglyceride levels, *Genet epidemiol*, 13(2):179-92 (1996).

Glock, Barbara et al., Allelic Ladder Characterization of the Short tandem Repeat Polymorphism in Intron 6 of the Lipoprotein Lipase Gene and Its Application in an Austrian Caucasian Population Study, *Journal of Forensic Sciences*, JFSCA, vol. 41, No. 4, pp. 579-581 (Jul. 1996).

Gotoda, Takanari et al., Detection of three separate DNA polymorphisms in the human lipoprotein lipase gene by gene amplification and restriction endonuclease digestion, *Journal of Lipid Research*, vol. 33, pp. 1067-1072 (1992).

Haffner SM, Stern MP, Hazuda HP, Pugh J, Patterson JK, Malina R. Upper body and centralized adiposity in Mexican Americans and non- Hispanic whites: relationship to body mass index and other behavioral and demographic variables. Int J Obes 1986;10:493-502.

Hanley AJ, Williams K, Stern MP, Haffner SM. Homeostasis model assessment of insulin resistance in relation to the incidence of cardiovascular disease: the San Antonio Heart Study. Diabetes Care 2002;25:1177-84.

Haseman JK, Elston RC. The investigation of linkage between a quantitative trait and a marker locus. Behav Genet 1972;2(1):3-19.

Holmer SR, Hengstenberg C, Mayer B, et al. Lipoprotein lipase gene polymorphism, cholesterol subfractions and myocardial infarction in large samples of the general population. Cardiovascular Research 2000;47:806-12.

Hong Y, Pedersen NL, Brismar K, de Faire U. Genetic and environmental architecture of the features of the insulin- resistance syndrome. Am J Hum Genet 1997; 60:143-52.

Jemaa R, Tuzet S, Portos C, Betoulle D, Apfelbaum M, Fumeron F. Lipoprotein lipase gene polymorphisms: associations with hypertriglyceridemia and body mass index in obese people. Int J Obes Relat Metab Disord 1995;19:270-4.

Lee, W.J., Sheu, W.H., Jeng, C.Y., Young, M.S., and Chen, Y.T. (2000) Associations between lipoprotein lipase gene polymorphisms and insulin resistance in coronary heart disease. Chung-Hua I Hsueh Tsa Chih [Chinese Medical Journal], 63, 563-572.

Livak, K.J. (1999) Allelic discrimination using fluorogenic probes and the 5' nuclease assay. Genet. Anal.: Biomolecular Engineering, 14, 143-149.

Malloy MJ, Kane JP. A risk factor for atherosclerosis: triglyceride-rich lipoproteins. Adv Intern Med 2001; 47:111-36.

Matthews DR, Hosker JP, Rudenski AS, Naylor BA, Treacher DF, Turner RC. Homeostasis model assessment: insulin resistance and beta-cell function from fasting plasma glucose and insulin concentrations in man. Diabetologia 1985:28:412-9.

Mattu RK, Needham EW, Morgan R, et al. DNA variants at the LPL gene locus associate with angiographically defined severity of atherosclerosis and serum lipoprotein levels in a Welsh population. Arterioscler Thromb 1994;14:1090-7.

Mead JR, Ramji DP. The pivotal role of lipoprotein lipase in atherosclerosis. Cardiovasc Res 2002;55:261-9.

Mitchell BD, Kammerer CM, Mahaney MC, et al. Genetic analysis of the IRS. Pleiotropic effects of genes influencing insulin levels on lipoprotein and obesity measures. Arterioscler Thromb Vasc Biol 1996; 16(2):281-8.

Mitchell, R. J. et al., DNA polymorphisms at the lipoprotein lipase gene and their association with quantitative variation in plasma high-density lipoproteins and triacylglycerides, *Hum Biol*, 66(3):383-97 (Jun. 1994). Abstract Only.

Minnich A. et al., Lipoprotein lipase gene mutations in coronary artery disease, *Can J. Cardiol*, 14(5):711-6 (May 1998). Abstract Only.

Motulsky AG, Brunzell JD. Genetics of coronary atherosclerosis. In: King RA, Rotter JI, Motulsky AG, eds. The Genetic Basis of Common Diseases. New York, NY: Oxford University Press, Inc., 2002:105-126.

Murthy V, Julien P, Gagne C. Molecular pathobiology of the human lipoprotein lipase gene. Pharmacol Ther 1996;70:101-135.

Nicklas, B.J., Ferrell, R.E., Rogus, E.M., Berman, D.M., Ryan, A.S., Dennis, K.E., and Goldberg, A.P. (2000) Lipoprotein lipase gene variation is associated with adipose tissue lipoprotein lipase activity, and lipoprotein lipid and glucose concentrations in overweight postmenopausal women. Hum. Genet., 106, 420-424.

O'Connell JR, Weeks DE. PedCheck: a program for identification of genotype incompatibilities in linkage analysis. Am J Hum Genet 1998;63:259-66.

Okosun IS, Liao Y, Rotimi CN, Prewitt TE, Cooper RS. Abdominal adiposity and clustering of multiple metabolic syndrome in White, Black and Hispanic Americans. Ann Epidemiol 2000;10:263-70.

Park YW, Zhu S, Palaniappan L, Heshka S, Camethon MR, Hymsfield SB. The metabolic syndrome: prevalence and associated risk factor findings in the US population from the Third National Health and Nutrition Examination Survey, 1988-1994. Arch Intern Med 2003;163:427-36.

Paulweber, Bernhard et al., Molecular basis of lipoprotein lipase deficiency in two Austrian families with type 1 hyperlipoprtoeinemia, *Atherosclerosis*, vol. 86, pp. 239-250 (1991).

Phillips DI, Caddy S, Ilic V, et al. Intramuscular triglyceride and muscle insulin sensitivity: evidence for a relationship in nondiabetic subjects. Metabolism 1996; 45(8):947-950.

Preiss-Landl K, Zimmerman R, Hammerle G, Zechner R. Lipoprotein lipase: the regulation of tissue specific expression and its role in lipid energy metabolism. Curr Opin Lipidol 2002;13:471-81.

Proenza AM, Poissonnet CM, Ozata M, et al. Association of sets of alleles of genes encoding beta3-adrenoreceptor, uncoupling protein 1 and lipoprotein lipase with increased risk of metabolic complications in obesity. Int J Obes Relat Metab Disord 2000;24:93-100.

Pyorala M, Miettinen H, Laakso M, Pyorala K. Hyperinsulinemia predicts coronary heart disease risk in healthy middle- aged men: the 22-year follow-up results of the Helsinki Policemen Study. Circulation 1998;98:398-404.

Rioux JD, Daly MJ, Silverberg MS, Lindblad K, Steinhart H, Cohen Z, Delmonte T, Kocher K, Miller K, Guschwan S, Kulbokas EJ, O'Leary S, Winchester E, Dewar K, Green T, Stone V, Chow C, Cohen A, Langelier D, Lapointe G, Gaudet D, Faith J, Branco N, Bull SB, McLeod RS, Griffiths AM, Bitton A, Greenberg GR, Lander ES, Siminovitch KA, Hudson TJ. Genetic variation in the 5q31 cytokine gene cluster confers susceptibility to Crohn disease. Nat Genet 2001;29:223-228.

Samuels ME, Forbey KC, Reid JE, et al. Identification of a common variant in the lipoprotein lipase gene in a large Utah kindred ascertained for coronary heart disease: the—93G/D9N variant predisposes to low HDL-C/high triglycerides. Clin Genet 2001;59:88-98.

Sobel E, Lange K. Descent graphs in pedigree analysis: applications to haplotyping, location scores, and marker-sharing statistics. Am J Hum Genet 1996;58:1323-1337.

Spielman RS, McGinnis RE, Ewens WJ. Transmission test for linkage disequilibrium: the insulin gene region and insulin-dependent diabetes mellitus (IDDM). Am J Hum Genet 1993;52:506-16.

Takagi, Atsuko et al., Identification of two new alleles at the lipoprotein lipase (LPL) short tandem repeat (STR) locus results in seven polymorphic alleles in the Japanese population: allele frequency data in comparison with Caucasian populations, *Molecular and Cellular Probes*, Vo. 10, pp. 227-228 (1996).

Templeton AR, Sing CF, Kessling A, Humphries S. A cladistic analysis of phenotype associations with haplotypes inferred from restriction endonuclease mapping. II. The analysis of natural populations. Genetics 1988;120:1145-1154.

Templeton AR. Cladistic approaches to identifying determinants of variability in multifactorial phenotypes and the evolutionary significance of variation in the human genome. Ciba Found Symp 1996;197:259-283.

Templeton, A.R., Weiss, K.M., Nickerson, D.A., Boerwinkle, E., and Sing, C.F. (2000) Cladistic structure within the human lipoprotein lipase gene and its implications for phenotypic association studies. Genetics, 156, 1259-1275.

Ukkola O, Garenc C, Perusse L, et al. Genetic variation at the lipoprotein lipase locus and plasma lipoprotein and insulin levels in the Quebec Family Study. Atherosclerosis 2001;158:199-206.

Wallace TM, Matthews DR. The assessment of insulin resistance in man. Diabet Med 2002;19:527-34.

Wu, D.A., Bu, X., Warden, C.H., Shen, D.D., Jeng, C.Y., Sheu, W.H., Fuh, M.M., Katsuya, T., Dzau, V.J., Reaven, G.M. et al. (1996) Quantitative trait locus mapping of human blood pressure to a genetic region at or near the lipoprotein lipase gene locus on chromosome 8p22. J. Clin. Invest., 97(9), 2111-2118.

* cited by examiner

SEQUENCE LISTING

<160> NUMBER OF SEQ ID NOS: 25

<210> SEQ ID NO 1
<211> LENGTH: 28
<212> TYPE: DNA
<213> ORGANISM: Artificial Sequence
<220> FEATURE:
<223> OTHER INFORMATION: Forward primer

<400> SEQUENCE: 1
tcaagtcatt aaaatcaatc tagccttt                                28

<210> SEQ ID NO 2
<211> LENGTH: 35
<212> TYPE: DNA
<213> ORGANISM: Artificial Sequence
<220> FEATURE:
<223> OTHER INFORMATION: Reverse primer

<400> SEQUENCE: 2
ttctctttag attttatatt ccatttttta ctatg                        35

<210> SEQ ID NO 3
<211> LENGTH: 25
<212> TYPE: DNA
<213> ORGANISM: Artificial Sequence
<220> FEATURE:
<223> OTHER INFORMATION: Forward primer

<400> SEQUENCE: 3
cctggataat caaagattca aacca                                   25

<210> SEQ ID NO 4
<211> LENGTH: 25
<212> TYPE: DNA
<213> ORGANISM: Artificial Sequence
<220> FEATURE:
<223> OTHER INFORMATION: Reverse primer

<400> SEQUENCE: 4
ggagacaggt tgagattatc ttgga                                   25

<210> SEQ ID NO 5
<211> LENGTH: 29
<212> TYPE: DNA
<213> ORGANISM: Artificial Sequence
<220> FEATURE:
<223> OTHER INFORMATION: Forward primer

<400> SEQUENCE: 5
cataaaatga attacacaga gatcgctat                               29

<210> SEQ ID NO 6
<211> LENGTH: 33
<212> TYPE: DNA
<213> ORGANISM: Artificial Sequence
<220> FEATURE:
<223> OTHER INFORMATION: Reverse primer

<400> SEQUENCE: 6
tcaatcctaa cttagagttt ttttaaatta aca                          33

<210> SEQ ID NO 7
<211> LENGTH: 24
<212> TYPE: DNA
<213> ORGANISM: Artificial Sequence
<220> FEATURE:
<223> OTHER INFORMATION: Forward primer

<400> SEQUENCE: 7
gtggcctgag tgtgacagtt aatt                                    24

<210> SEQ ID NO 8
<211> LENGTH: 25

```
<212> TYPE: DNA
<213> ORGANISM: Artificial Sequence
<220> FEATURE:
<223> OTHER INFORMATION: Reverse primer

<400> SEQUENCE: 8
atcaaaagca ctgttcacaa aggta                                              25

<210> SEQ ID NO 9
<211> LENGTH: 23
<212> TYPE: DNA
<213> ORGANISM: Artificial Sequence
<220> FEATURE:
<223> OTHER INFORMATION: Forward primer

<400> SEQUENCE: 9
ttgtgaaatg ccatgacaag tct                                                23

<210> SEQ ID NO 10
<211> LENGTH: 21
<212> TYPE: DNA
<213> ORGANISM: Artificial Sequence
<220> FEATURE:
<223> OTHER INFORMATION: Reverse primer

<400> SEQUENCE: 10
ccagtcagct ttagcccaga a                                                  21

<210> SEQ ID NO 11
<211> LENGTH: 20
<212> TYPE: DNA
<213> ORGANISM: Artificial Sequence
<220> FEATURE:
<223> OTHER INFORMATION: Forward primer

<400> SEQUENCE: 11
tccatgtggc agctgttagc                                                    20

<210> SEQ ID NO 12
<211> LENGTH: 27
<212> TYPE: DNA
<213> ORGANISM: Artificial Sequence
<220> FEATURE:
<223> OTHER INFORMATION: Reverse primer

<400> SEQUENCE: 12
gagtagtgaa ggtcacatgc ttagtgt                                            27

<210> SEQ ID NO 13
<211> LENGTH: 17
<212> TYPE: DNA
<213> ORGANISM: Artificial Sequence
<220> FEATURE:
<223> OTHER INFORMATION: Probe

<400> SEQUENCE: 13
cctgggtttc ctacaat                                                       17

<210> SEQ ID NO 14
<211> LENGTH: 17
<212> TYPE: DNA
<213> ORGANISM: Artificial Sequence
<220> FEATURE:
<223> OTHER INFORMATION: Probe

<400> SEQUENCE: 14
```

```
cctgggtttc ctagaat                                              17
```

<210> SEQ ID NO 15
<211> LENGTH: 17
<212> TYPE: DNA
<213> ORGANISM: Artificial Sequence
<220> FEATURE:
<223> OTHER INFORMATION: Probe

<400> SEQUENCE: 15

```
ctcacccttc ttgaaga                                              17
```

<210> SEQ ID NO 16
<211> LENGTH: 16
<212> TYPE: DNA
<213> ORGANISM: Artificial Sequence
<220> FEATURE:
<223> OTHER INFORMATION: Probe

<400> SEQUENCE: 16

```
tcacccttct ggaaga                                               16
```

<210> SEQ ID NO 17
<211> LENGTH: 18
<212> TYPE: DNA
<213> ORGANISM: Artificial Sequence
<220> FEATURE:
<223> OTHER INFORMATION: Probe

<400> SEQUENCE: 17

```
cacatttagt ataaaagc                                             18
```

<210> SEQ ID NO 18
<211> LENGTH: 18
<212> TYPE: DNA
<213> ORGANISM: Artificial Sequence
<220> FEATURE:
<223> OTHER INFORMATION: Probe

<400> SEQUENCE: 18

```
cacatttagt ataaacgc                                             18
```

<210> SEQ ID NO 19
<211> LENGTH: 18
<212> TYPE: DNA
<213> ORGANISM: Artificial Sequence
<220> FEATURE:
<223> OTHER INFORMATION: Probe

<400> SEQUENCE: 19

```
agcatgatca tgtattat                                             18
```

<210> SEQ ID NO 20
<211> LENGTH: 19
<212> TYPE: DNA
<213> ORGANISM: Artificial Sequence
<220> FEATURE:
<223> OTHER INFORMATION: Probe

<400> SEQUENCE: 20

```
cagcatgatc atgtagtat                                            19
```

<210> SEQ ID NO 21
<211> LENGTH: 13
<212> TYPE: DNA
<213> ORGANISM: Artificial Sequence

```
-continued

<220> FEATURE:
<223> OTHER INFORMATION: Probe

<400> SEQUENCE: 21
ccagcctgac ttc                                                          13

<210> SEQ ID NO 22
<211> LENGTH: 14
<212> TYPE: DNA
<213> ORGANISM: Artificial Sequence
<220> FEATURE:
<223> OTHER INFORMATION: Probe

<400> SEQUENCE: 22
accagcctca cttc                                                         14

<210> SEQ ID NO 23
<211> LENGTH: 15
<212> TYPE: DNA
<213> ORGANISM: Artificial Sequence
<220> FEATURE:
<223> OTHER INFORMATION: Probe

<400> SEQUENCE: 23
ccagagcgtc agtac                                                        15

<210> SEQ ID NO 24
<211> LENGTH: 15
<212> TYPE: DNA
<213> ORGANISM: Artificial Sequence
<220> FEATURE:
<223> OTHER INFORMATION: Probe

<400> SEQUENCE: 24
ccagagcatc agtac                                                        15

<210> SEQ ID NO 25
<211> LENGTH: 9734
<212> TYPE: DNA
<213> ORGANISM: Homo sapiens

<400> SEQUENCE: 25
tgtaacacaa aattaaaata agtagaatta gttttcagta tttcctatat ttggaaaaca         60
atatttatat tcattttgtt tcttttagtt ttattttttgg cagaactgta agcaccttca       120
ttttcttttt cttccaaagg aggagtttaa ctaccctctg acaatgtcc atctcttggg        180 atacagcctt ggagcccatg ctgctggcat tgcaggaagt ctgaccaata agaaagtcaa       240
cagaattact ggtaagaaag caatttcgtt ggtcttatca taagaggtga aaagactgtc       300
attctgagag agaatcagaa caaattttgt taaatacca catgtgtggt gttcttccg         360 gagacatgac cagcacttga ttatctcatt gtagggctct ttattaggga taagaaaaaa       420
cacagacgct ctcactggct tactatccac tggcaatagc acagaaataa agcataatta       480
cacacaatgc ctgcagattt ctctgggaag cctgtttcct cccactctca gctctgtgtt       540
ttagtagtgt aaatgcacat cagtactagg agaaaagaag aaggaccaat tccagaggcc       600
acttcgaaag aagaccgtca tctaggcaaa ggtgtggcat acacagag agaaagaacc         660 caccactgtt tatacatctt ctcgacatat tcagaaataa tctacaaaag gaaatccagc       720
catcctgagt ggaaattgct gcataaggct agtttaagag actcaaattc attttagaag      780
gagccaagcc tccttttatg tctctctaag taaagatacc atgactgtag aataggagct       840
```

```
aataagaatc taaatagctg ccagtgcatt caaatgatga gcagtgacat gcgaatgtca      900
tacgaatgga aatttacaaa tctgtgttcc tgcttttttc ccttttaagg cctcgatcca      960
gctggaccta actttgagta tgcagaagcc ccgagtcgtc tttctcctga tgatgcagat     1020
tttgtagacg tcttacacac attcaccaga gggtcccctg gtcgaagcat tggaatccag     1080
aaaccagttg ggcatgttga catttacccg aatggaggta cttttcagcc aggatgtaac     1140
attggagaag ctatccgcgt gattgcagag agaggacttg gaggtaaata ttatttagaa     1200
gcgaattaaa tgtgactctt atccttaacc cttattgacc caatgtccta ctcagtagct     1260
tcaaagtatg tagttttcat atacacattt ggccaaatta tgtttctgaa gaattctgca     1320
atgttcagca tgaccacctt agagccaggc agacagccat tttatctttt atttactata     1380
ctgtaggcta cactgagcag tgcacttaca gtagcaagag aaaaaggtgg gattttagac     1440
aggaagactc cactgacctc aataatggca tcataaaatg ctatctggcc acatgttgtc     1500
ataccttgaa tgtagctgca aagccaatgg aaagatttta gatgttactg aacagaaga     1560 tgttaattag cataaatctt ccaaaatgtt cagaacataa tgttagctta atgttttact     1620
ttaataatgt tagcttgtgt taaatttatg attttttgttt gtttgttttt tgagatagag     1680
tcttattcta ttgcccaagc tggggtgcag tcacacaatc acagggactt gcaatgttgc     1740
ccaggctggt ctcaaactcc tggcctcaag tgatcctcct gcctcagcct cccaaagttc     1800
tgggattgca gctgtgagcc accacgccca gtttacgatt tatttttaag agccccttgc     1860
atactttata gacattggga cctacctagg atattctcgt tattttttgtg cacgtaatag     1920 aacttagagc atattgttac tattttcgat tgtcctaaaa acttacaagg aattcattct     1980
tatggcattg ctgattattt ctatgttcat ttgatataaa agagtgttag taggggcaga     2040
accctcaatt gtacataata tcaatgataa aatacaattc atttaacaat taccctctta     2100
agatgtggtt tctagaaata caaattgtcc ctaacttaca gttttccaac tttacaattg     2160
ggctgtaaca ccatttttaag ttgagaagca cgtgatggtt tgacttaaaa cttttttgaca     2220 ttatgatggg ttttgggggt attaagtgca ttttgactta cagtattttt gacttatgaa     2280
gaatttattg taaggcaagg ggcaggtata tgtttctaga agcacctaga agtgttagac     2340
actttcaatg taagagaagg atgagataaa caaggaaatc acacctccac cttggaggct     2400
tattacagct tcataaacat actcataaat ataagaagca caaagtcaa aaattccctg     2460 tgaacttgca actttcactc tcttgaaggt gggtgggccg ctaccaccaa gaatatctcc     2520
tgaaataggg cctacaatca taaatgcaca ggactatatc cttgggtgat tctactctaa     2580
caccacatct cacctatttt agacatgcca aatgaaacac tctttgtgaa tttctgccga     2640
gatacaatct tggtgtctct ttttaccca gatgtggacc agctagtgaa gtgctcccac     2700
gagcgctcca ttcatctctt catcgactct ctgttgaatg aagaaaatcc aagtaaggcc     2760
tacaggtgca gttccaagga agcctttgag aaagggctct gcttgagttg tagaaagaac     2820
cgctgcaaca atctgggcta tgagatcaat aaagtcagag ccaaaagaag cagcaaaatg     2880
tacctgaaga ctcgttctca gatgccctac aaaggtaggc tggagactgt tgtaaataag     2940
gaaaccaagg agtcctattt catcatgctc actgcatcac atgtactgat tctgtccatt     3000
ggaacagaga tgatgactgg tgttactaaa ccctgagccc tggtgtttct gttgataggg     3060
ggttgcattg atccatttgt ctgaggcttc taattcccat tgtcagcaag gtcccagtgc     3120
tcagtgtggg atttgcagcc ttgctcgctg ccctcccctg taaatgtggc cattagcatg     3180
ggctaggcta tcagcacaga gctcagagct catttggaac catccacctc gggtcaacaa     3240
```

-continued

```
actataaccc ttgtgccaaa tccagcctac ttcctgcttt tgtaaatagt tttttttaaaa    3300
cttttaagtt cagggGtacg tatgtaggtt tgctaaaaag gtaaacttgt gacatgggag    3360
tttgttgtcc agaatattcc atcacccagg tattaagctt agtacccatt agttactttt    3420
cctgaagctc tccctcctcc caccctctgg gaggcccag tgtctgttgt tccctctat    3480
gtgctcatgc aaagttttat taggacacag ccacacacat tcattaccat attgtcaaag    3540
gctggtttca tgccaccata acagagttga tagcccacag agcctaaaat atttactccc    3600
tggcccttta cagaatgttc acaacttaca taaaggcaag gaccatctgt cttatttatt    3660
tatttattta atttgagatg aagtctagct ttctcctagg ctggaggaga ggggcatgat    3720
cttggctcac cacaacctct gcctcccggg ttcaaatgat tccctgcct cagcctccgg    3780
agtagctggg ataacaggca tgcaccatca tgcccagcta attttgtat ttttagtaga    3840
gagggggttt caccgtgttg accaggctgg tctcgaactg ctgacctcag gtgatctgcc    3900
ctccttggcc tcatctgtct ttttaaatgc aactattcct ggaaggcaag aatatctcac    3960
accttctaag atactgccat tttgccagga gtttgtttca cacttgaatt tcaagcttgg    4020
cctcttgttt agaggcagac ctaaaggaat ggtcggaaaa tgagagagga ggtcttcgga    4080
taaatccggt gagagggacc aacttcagga agggtggctt ttgtggaatc cagatggaaa    4140
cctgagggaa gggatgatat taaagaacag tggccccagg taaaacatat ggcacccatg    4200
tgtaaggtga ttcttagaat ctgtagaggt gtctttcgtg gtatagaggt tgaggcacct    4260
gtgcttcaag gaaaccttaa ctcttcaaaa tcaggcaatg cgtatgaggt aaagagagga    4320
ctgtgggacc ataatcttga agacacagac aggcttcact catccctgcc tcctgcacca    4380
gtgggttcaa ggctctgtca gtgtcccta ggggcacctc accactccca gcttcttcag    4440
ctctggcctg tcctgctgcc tgcaagggtt ttgcttaatt ctcaattcaa tgtctcttca    4500
tcttttagta gctgtggggt tttgttgttg ttcttctgtt tttgcttagt atctgactac    4560
ttttttaatta taaaaagaga tgtatctaaa caaaatagag attgttatca gaagttcaca    4620
acatttatta aaaatttttt cacctggaca agagtctaaa gcagcataaa aatatggtct    4680
gctatattct aaaccatcag tcttaagaga tctgtgtctc agcttaagag aaaatacatt    4740
taatagacag taacacaaat aagaaaaaaa tctgaccaag gatagtggga tatagaagaa    4800
aaaacattcc aagaattatt ttatttattt atttatttat ttatttattt atttatttat    4860
ttttgagaca cggtctcgct cagttaccca ggctggagtg cagcggcgca atcttaactc    4920
actgcaacct ctgctttccg gttcaagcga ttctcctgcc tcagcctcct gagtaactgg    4980
gattacaggc acccgccacc acgcccaact aatttctgta ttttttcttag tagaaacagg    5040
gtttcaccat gttggccaag ctagtctcaa actcctgacc tcaggtgatt cacccaccaa    5100
ggcctcccaa agtgctggga ttacaggcat gagccaccat gcctggcctc caaaaactct    5160
tttttcctcc atcatcatgg ttctatttta gtcctgctgc ctttccttt aacctctccc    5220
caggcccatt tgctcaggt ttttggtaga accagagga ggggcaggga ggagatatag    5280
aagttcaact acctgcttcc agaggctgtc cctagtatag aatactttag gggctggctt    5340
tacaaggcag tccttgtggc ctcactgatg gctcaatgaa ataagttctt ttttaaaaaa    5400
aattttattt atttccatag gttattgggg gaacaggtgg tgtttggtta catgagtaag    5460
ttctttagta gtgatttgtg agattttggt gtgcccatta cggaatggaa aaatcaacga    5520
aataagttct atgatgcacc tactagacac ctaatctgca ctagatggtg ggggaattaa    5580
```

-continued

```
gagcatgggc atgatcctgt gaccggaagc ccgcttacag tcaggtggga ggacagacct      5640
actcatgaaa caaacacagt gacatatagt gacacagaag caaatgtcaa atatgcttgc      5700
tccagatgct aaggcacaag atggccaagg atggcggagt tcatggagaa agcatcatga      5760
gtgttttggc cttctgattt gatctcccta gcacccctca agatggcta cttcctaatg       5820 ctgcttggca attcagacac atttgggttt ttcctatgca taaccaca cttttctgaa        5880 agggagtaga attcaaggtc tgcattttct aggtatgaac actgtgcatg atgaagtctt      5940
tccaagccac accagtggtt ccatgtgtgt gcacttccgg tttgagtgct agtgagatac      6000
ttctgtggtt ctgaattgcc tgactatttg gggttgtgat attttcataa agattgatca      6060
acatgttcga atttcctccc caacagtctt ccattaccaa gtaaagattc attttctgg       6120 gactgagagt gaaacccata ccaatcaggc ctttgagatt tctctgtatg caccgtggc       6180 cgagagtgag aacatcccat tcactctgtg agtagcacag ggggcggtc atcatggcac       6240 cagtccctcc cctgccataa cccttggtct gagcagcaga agcagagagc gatgcctaga      6300
aaacaagtct ttagttaaaa aaatcagaat ttcaaaattg aggtctttcc tctatttgat      6360
attgagaaaa aaatgcttca aattggccat tttattttca cttactagtt atattttttt      6420
atttatcatc ttatatctgt ttatttcttt tataaagctg ctgttaaaca atataattaa      6480
actatctcaa aaggtttgac attaaagaaa atgagcaatg gtaacaggaa accactctat      6540
agatgtacat ataatatgta cagaaaatat aagtagtaag aagtccatga caaagtgtta      6600
gctctttttt tttttttttt tttttttttt tttgagatgg agtctctctc ctattgccca      6660
ggctggagtg cagtgattcg atctcagctc actgcaacct ctacctcccg agttcaaaca      6720
attcttctgt ctcagcctcc cgagtagctg gggctgcagg tgcccaccac catgcccagc      6780 taattttgt attttagta gcgacgggt ctcaccatgt tggccaagct ggtcttgaat         6840
tcctgatctc aggtgatcca cccgcctcgg cctcccaaag tgctgggatt acaggtgtga      6900
gccaccatgc ccagcctacc ctttactact aatcaaagaa ataaagtaa ggcaacttga       6960 tactttaca attactagat gaacaaatct ttaaaaatag ccagtgcaga caaggtggtg       7020
aagcagaaca tgcgaaccta ccatgcatca ttcacggcta gaaccctcca ggtgcggaag      7080
gtagtatttt ataacttttc catagctaca aatatattatt acatagaagg gagtgatttt     7140
tttctaatat ttatcctaaa gaaatagtca acaaacattt ttaaaaaaca tcaattacag      7200
tcgtacctat actagcataa attagaaacc cagtatccaa cattgaggca gtgggtaaat      7260
gaatcgtggt ttatcaagtc attaaaatca atctagcctt taaaaactat aattgtagga      7320
aacccaggaa aacatagtaa aaaatggaat ataaaatcta aagagaataa agaatagaga      7380
atcgtatgtg tgctatgatt gtagctaaat aatgttcaag tatcaacaca aattgaaaag      7440
gaatacatga aaatgaaaat tatatttctg aatgattgac ttcaggattt tcttttagaa      7500
ttgtattaaa tagttcatgt cattaggata aatgctggaa tgtggatata atttaaaata      7560
tactaaatgc catcgacctt cattttgagt tctttgttgg acattttgt gcatttttaa       7620 aatatcccct aaataataaa gctatttata tttggagagg agaaaaaaaa gtgggggca       7680 gggagagctg atctctataa ctaaccaaat ttattgcttt tttgtttagg cctgaagttt      7740
ccacaaataa gacatactcc ttcctaattt acacagaggt agatattgga gaactactca      7800
tgttgaagct caaatggaag agtgattcat actttagctg gtcagactgg tggagcagtc      7860
ccggcttcgc cattcagaag atcagagtaa agcaggaga gactcagaaa aagtaattaa       7920
atgtattttt cttccttcac tttagacccc cacctgatgt caggacctag ggctgtatt       7980
```

```
tcagggcct tcacaattca gggagagctt taggaaacct tgtatttatt actgtatgat    8040
gtagattttc tttaggagtc ttcttttatt ttcttatttt tgggggcgg gggggaagt     8100 gacagtattt ttgtatttca tgtaaggaaa acataagccc tgaatcgctc acagttattc    8160
agtgagagct gggattagaa gtcaggaatc tcagcttctc atttggcact gtttcttgta    8220
agtacaaaat agttagggaa caaacctccg agatgctacc tggataatca aagattcaaa    8280
ccaacctctt caagaagggt gagattccaa gataatctca acctgtctcc gcagcccac    8340 ccatgtgtac ccataaaatg aattacacag agatcgctat aggatttaaa gcttttatac    8400
taaatgtgct gggattttgc aaactatagt gtgctgttat tgttaattta aaaaaactct    8460
aagttaggat tgacaaatta tttctctta gtcatttgct tgtatcacca agaagcaaa     8520 caaacaaaca aaaaaaaaa gaaaagatc ttgggatgg aaatgttata agaatcttt      8580 tttacactag caatgtctag ctgaaggcag atgccctaat tccttaatgc agatgctaag    8640
agatggcaga gttgatcttt tatcatctct tggtgaaagc ccagtaacat aagactgctc    8700
taggctgtct gcatgcctgt ctatctaaat taactagctt ggttgctgaa caccgggtta    8760
ggctctcaaa ttaccctctg attctgatgt ggcctgagtg tgacagttaa ttattgggaa    8820
tatcaaaaca attacccagc atgatcatgt attatttaaa cagtcctgac agaactgtac    8880
ctttgtgaac agtgcttttg attgttctac atggcatatt cacatccatt ttcttccaca    8940
gggtgatctt ctgttctagg gagaaagtgt ctcatttgca gaaaggaaag gcacctgcgg    9000
tatttgtgaa atgccatgac aagtctctga ataagaagtc aggctggtga gcattctggg    9060
ctaaagctga ctgggcatcc tgagcttgca ccctaaggga ggcagcttca tgcattcctc    9120
ttcaccccat caccagcagc ttgccctgac tcatgtgatc aaagcattca atcagtcttt    9180
cttagtcctt ctgcatatgt atcaaatggg tctgttgctt tatgcaatac ttcctctttt    9240
tttctttctc ctcttgtttc tcccagcccg gaccttcaac ccaggcacac attttaggtt    9300
ttattttact ccttgaacta cccctgaatc ttcacttctc cttttttctc tactgcgtct    9360
ctgctgactt tgcagatgcc atctgcagag catgtaacac aagtttagta gttgccgttc    9420
tggctgtggg tgcagctctt cccaggatgt attcagggaa gtaaaaagat ctcactgcat    9480
cacctgcagc cacatagttc ttgattctcc aagtgccagc atactccggg acacacagcc    9540
aacagggctg ccccaagcac ccatctcaaa accctcaaag ctgccaagca aacagaatga    9600
gagttatagg aaactgttct ctcttctatc tccaaacaac tctgtgcctc tttcctacct    9660
gacctttagg gctaatccat gtggcagctg ttagctgcat cttccagag cgtcagtact     9720 gagaggacac taag                                                     9734
```

METHOD OF HAPLOTYPE-BASED GENETIC ANALYSIS FOR DETERMINING RISK FOR DEVELOPING INSULIN RESISTANCE AND CORONARY ARTERY DISEASE

This application claims the benefit of U.S. provisional application 60/388,726, filed Jun. 14, 2002.

The U.S. Government has a paid-up license in this invention and the right in limited circumstances to require the patent owner to license others on reasonable terms as provided for by the terms of Contracts HL-60030, HL-67974, and HL-69757, awarded by the National Institutes of Health and NRSA Training Grant 5 T32 GM08243-16.

BACKGROUND OF THE INVENTION

1. Field of the Invention

The present invention relates to the field of medical genetics.

2. Discussion of the Related Art

The insulin resistance syndrome (also called the metabolic syndrome) is a clustering of factors associated with an increased risk of coronary artery disease (CAD; 21). The syndrome affects over 20% of adults in the United States, with the highest age-specific prevalence rates in Mexican-Americans (22). Insulin resistance, whether or not it is accompanied by other features of the metabolic syndrome, has been associated with an increased risk of cardiovascular events and death (23, 24).

There is evidence in the Framingham offspring study that three factors or syndrome clusters, underlie the clustering of basic risk variables that form the insulin resistance syndrome: a diabetic predisposing syndrome characterized by impaired glucose tolerance, a cardiovascular metabolic syndrome, and a hypertension syndrome. Numerous lines of evidence from epidemiological studies support the idea that these factors occur many years prior to the onset of overt coronary artery disease.

The clustering of insulin resistance, hypertension, central obesity, and dyslipidemia in the metabolic syndrome is receiving much attention as a risk factor for cardiovascular disease. The central component of this syndrome, insulin resistance, has been found to increase cardiovascular risk. In the San Antonio Heart Study, insulin resistance, estimated by homeostatic model assessment (HOMA), was an independent predictor of incident cardiovascular events over 8 years of follow-up (24). In the Helsinki Policemen Study, 970 men free of diabetes or CAD at baseline were followed for 22 years; those with the highest levels of insulin resistance as estimated by insulin area under the curve during oral glucose tolerance testing had the highest rates of CAD events and death (23). High fasting insulin concentrations were an independent predictor of ischemic heart disease events among 2103 non-diabetic Canadian men (51). A genetic basis for the components of the insulin resistance syndrome has been demonstrated by familial aggregation (52, 53). For this reason, investigators have asked the question as to whether genetic determinants of insulin resistance also influence the other components of the metabolic syndrome (54).

As an example, lipoprotein lipase (LPL) plays a major role in lipid metabolism. Located on capillary endothelium, LPL hydrolyzes triglycerides of chylomicrons and very low density lipoproteins, generating free fatty acids and monoacylglycerol. Complete deficiency of LPL results in the familial chylomicronemia syndrome. Because LPL activity affects the concentration of triglycerides, an important cardiovascular risk factor, LPL has been studied as a candidate gene for atherosclerosis. Several studies have identified linkage and association of the LPL gene with hypertension (25, 1), indirect or surrogate measurements of insulin resistance (2, 3), dyslipidemia (2, 26, 27), obesity (28), and atherosclerosis (4, 29, 30). LPL is an excellent candidate connecting insulin resistance to atherosclerosis because it controls the delivery of free fatty acids (FFA) to muscle, adipose tissue, and vascular wall macrophages, wherein lipid uptake influences peripheral insulin sensitivity, central obesity, and foam cell formation (31, 32).

Wu et al demonstrated linkage of the LPL locus to systolic blood pressure in non-diabetic relatives of Taiwanese subjects with type 2 diabetes (1). The HindIII polymorphism in intron 8 of the LPL gene has been associated with measurements of insulin resistance in normoglycemic Caucasian and Hispanic subjects (2) and Chinese subjects (3). The Ser447Stop polymorphism has been found to be associated with decreased atherosclerosis risk (4). Both the HindIII and Ser447Stop polymorphisms are in the 3' end of the LPL gene, downstream of a recombination hotspot (5).

The LPL gene has emerged as a candidate gene for features of metabolic syndrome, including insulin resistance. LPL hydrolyzes triglycerides carried in chylomicrons and very low density lipoproteins, the rate-limiting step in delivery of free fatty acids (FFA) to muscle and adipose tissue. By controlling the delivery of FFA to muscle, LPL may affect insulin sensitivity by influencing levels of intramyocellular lipid, which correlate with muscle insulin resistance (55, 56). Also, LPL may influence insulin resistance by affecting FFA delivery to visceral adipose tissue, which is increasingly viewed as an endocrine organ, capable of secreting mediators of insulin resistance (57). LPL action also regulates the plasma triglyceride concentration, an important atherosclerosis risk factor (58, 59). LPL activity indirectly raises HDL-cholesterol levels because LPL-mediated hydrolysis of VLDL provides surface components that merge with HDL3 to form HDL2 particles (60). LPL-mediated delivery of FFA and lipoprotein remnants to vessel wall macrophages plays a role in foam cell formation, an early event in the development of atherosclerotic plaque (32). Thus, functional variation in LPL may impact both insulin resistance and atherosclerosis.

Most studies that have reported association of the LPL gene with insulin resistance used only surrogate measurements of insulin resistance, including fasting glucose (8, 33), fasting insulin (2, 34–36), and insulin area under the curve (AUC) during oral glucose tolerance testing (OGTT; 37). One study evaluated the steady state plasma glucose during the insulin suppression test (3). In addition, all except one (36) of these studies only examined association of the intronic restriction fragment length polymorphisms PvuII and HindIII. Thus, current evidence that variation in LPL plays a role in insulin sensitivity has been indirect. Assessment of glucose infusion rate (GINF) during the euglycemic hyperinsulinemic clamp study is widely regarded as the most direct physiologic measurement of insulin sensitivity (28, 29). An analysis of indices of insulin sensitivity in the Insulin Resistance Atherosclerosis Study showed that direct physiologic measurements of insulin sensitivity have a higher heritability than measures based on fasting values (such as HOMA; 61). Thus, use of physiologic indices rather than simple fasting indices should provide more power to discover genes that contribute to insulin sensitivity.

While various polymorphisms in the 3' end of LPL, such as HindIII, have been associated with surrogate measures of insulin resistance and with atherosclerosis (2, 3, 29, 30), published reports of positive linkage or association of variation in LPL with indices of insulin sensitivity have typically examined only one or two single nucleotide polymorphisms (e.g., 2, 3, 8, 33–37). However, a haplotype-based analysis recently demonstrated an association of LPL 3' end haplotypes with coronary artery disease in Mexican-Americans (30).

Published studies reporting association of the LPL gene with insulin resistance used only single variants, usually HindIII or PvuII (2, 3, 8, 33–37). In some cases, the results are in conflict; studies have reported the T allele of HindIII associated with insulin resistance (2), others report the G allele associated with insulin resistance (3, 37), and others show no association of HindIII with insulin resistance (8). This demonstrates a limitation of the common approach of examining one or two polymorphisms per candidate gene in an association study.

With the sequencing of the human genome it has become apparent that variation in individuals is quite extensive. There is increasing evidence that this variation is best described by groups of associated polymorphisms referred to as haplotypes (13–15).

Recent studies suggest that the extensive variation in human beings is best described by groups of associated polymorphisms referred to as haplotypes (13–15). Haplotypes encompass chromosomal blocks that have remained unbroken by recombination during the population evolutionary history of the gene. Haplotypes are more likely to identify disease associations than single polymorphisms because they reflect global gene structure and encompass the majority of common variation in a gene. Identification of a haplotype associated with increased or decreased disease risk should facilitate identification of the actual functional variant that affects disease risk, because this variant should lie on chromosome regions identified by that haplotype (17).

Thus, haplotypes capture the majority of common variation in a gene; consequently, the use of haplotypes is more likely to identify disease-variation associations than is the use of a random single polymorphism. Identification of a haplotype associated with increased or decreased disease risk should facilitate identification of the actual functional variant that affects disease risk, because this variant should lie on chromosomes identified by that haplotype (16, 17). Genotyping to determine haplotype structure and frequencies is required for this type of analysis. A major challenge is determination and selection of the polymorphisms that will be used to determine haplotypes in a given population.

Currently there is much interest in the use of haplotype data in the genetics of common diseases, such as coronary artery disease and insulin resistance. Investigators are faced with the considerable challenge of how many and which variants or markers to genotype in a given candidate gene for haplotype determination. Gabriel et al (15) sequenced 13 megabases across the genome in subjects from Africa, Europe, and Asia; it was shown that the human genome is organized in haplotype blocks (most of which are longer than 10 kilobases), with three to five commonly occurring (>5%) haplotypes per block. Only six to eight variants were sufficient to define the most common haplotypes in each block. There is a need for a way to select these variants, or markers, efficiently and affordably.

Accordingly, the present invention provides such a method of selecting useful haplotypes, as well particular haplotypes useful for predicting predisposition to insulin resistance in Mexican-Americans. These and other benefits are described hereinbelow.

SUMMARY OF THE INVENTION

The present invention relates to a method for determining haplotypes useful for application to large-scale genetic analysis and screening tests for a human subpopulation, such as Mexican-Americans, within a genomic reference sequence of interest. The method involves detecting the presence of a plurality of genetic markers, or variants, at positions of the genomic reference sequence, in the genotypes of a first number of subjects in the human subpopulation. A frequency hierarchy of the detected markers is identified, and from the frequency hierarchy a set of haplotypes is constructed, each haplotype of the set comprising at least one of the most frequently detected markers. A smaller subset of the set of haplotypes is selected, the smaller subset comprising those haplotypes most frequently occurring in the first number of subjects. The markers needed to define the thus selected smaller subset of the set of haplotypes is identified.

In some embodiments of the present invention, useful in determining genetic associations between specific haplotypes and particular phenotypes, a second number of subjects in the human subpopulation are genotyped for the markers previously identified in accordance with the method; the second number of subjects being larger than the first number of subjects. The genotypes of the second number of subjects are evaluated for any statistically significant association of any members of the thus selected smaller subset of the set of haplotypes with a phenotype of interest, which can be a disease or medical disorder, such as insulin resistance or coronary artery disease.

In accordance with the invention, a method of detecting a genetic predisposition in a Mexican-American human subject for developing insulin resistance is provided. The method involves collecting a biological sample from the subject; genotyping the sample at nucleotide positions 7315, 8292, 8393, 8852, 9040, and 9712, with respect to the Nickerson reference sequence of the human lipoprotein lipase gene (SEQ ID NO: 25) (see Table 1 hereinbelow); and assessing whether a haplotype (designated herein "haplotype 4"; see, e.g., Table 5) is present in the sample. The haplotype comprises the following (nucleotide position: variant allele): (i) 7315: G; (ii) 8292: A; (iii) 8393: G; (iv) 8852: G; (v) 9040: G; and (vi) 9712: G. The presence of the haplotype indicates a genetic predisposition for developing insulin resistance in the Mexican-American subject, as demonstrated hereinbelow.

Similarly, in accordance with an inventive method of detecting a lower than normal risk in a Mexican-American human subject for developing insulin resistance, the presence in the genotyped sample, instead, of a haplotype comprising (nucleotide position:variant allele): (i) 7315: G; (ii) 8292: A; (iii) 8393: T; (iv) 8852: T; (v) 9040: C; and (vi) 9712: G (designated herein "haplotype 1"; see, e.g., Table 5), indicates a lower than normal risk for developing insulin resistance in the subject, as demonstrated hereinbelow.

Alternatively, in accordance with the invention, a method of detecting a lower than normal risk in a Mexican-American human subject for developing coronary artery disease is provided. The method involves collecting a biological sample from the subject; genotyping the sample at nucleotide positions 7315, 8292, 8393, 8852, 9040, and 9712, with respect to the Nickerson reference sequence of the human lipoprotein lipase gene (SEQ ID NO: 25); and assessing whether the sample is homozygous for a haplotype comprising (nucleotide position:variant allele): (i) 7315: G; (ii) 8292:A; (iii) 8393: T; (iv) 8852: T; (v) 9040: C; and (vi) 9712: G (designated herein "haplotype 1"; see, e.g., Table 5). Homozygosity for haplotype 1 indicates a lower than normal risk for developing coronary artery disease in the subject.

If a greater than normal, or lower than normal, risk of developing insulin resistance or coronary artery disease is detected, in accordance with the invention, then suitable treatment or prophylactic modalities can be chosen, as appropriate for the individual with the benefit of this additional clinical information.

The meanings of abbreviations found herein are the following: LPL, lipoprotein lipase; CAD, coronary artery disease; MACAD, Mexican-American Coronary Artery Disease project; SNP, single nucleotide polymorphism; GINF, glucose infusion rate; $S_I$, insulin sensitivity.

The present invention is further described by U.S. provisional application 60/388,726, filed Jun. 14, 2002, the disclosures of which are incorporated by reference.

DETAILED DESCRIPTION OF THE PREFERRED EMBODIMENTS

Figure 1:
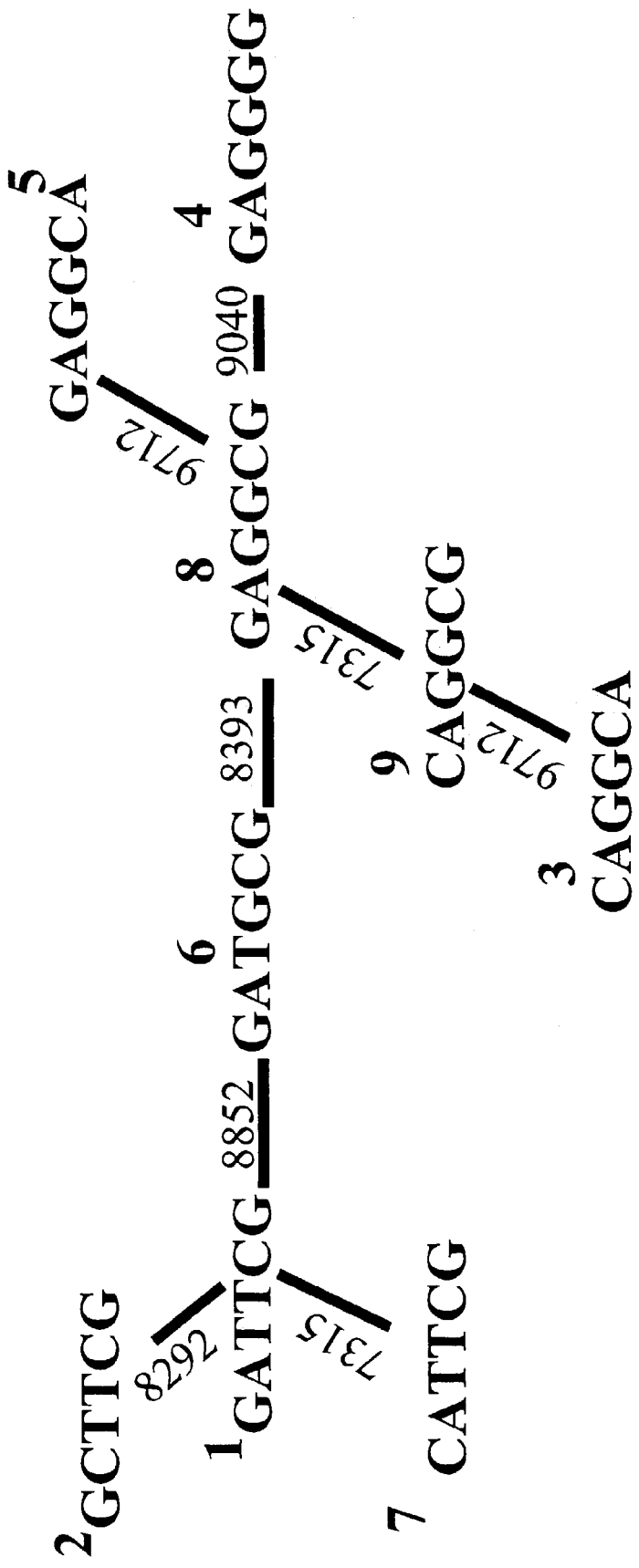
FIG. 1 illustrates the cladistic structure of the LPL 3'-end haplotypes. The lines connecting the haplotypes indicate a single nucleotide difference between the connected haplotypes, with the corresponding variant number above the line. The haplotypes are numbered in order of decreasing frequency. Haplotypes 1, 2, 6, and 7 contain HindIII allele 1; haplotypes 3, 4, 5, 8, and 9 contain contain HindIII allele 2.

The present invention is directed to a method for determining haplotypes within a genomic reference sequence of interest, which haplotypes are useful for large-scale genetic analysis and genetic screening tests for a human subpopulation. The genomic reference sequence of interest can be any coding or non-coding sequence of interest, for example, the human lipoprotein lipase (LPL) gene.

The LPL gene is located on the short arm of human chromosome 8, at 8p22. (R. S. Sparkes et al., *Human genes involved lipolysis of plasma lipoproteins: Mapping of loci for lipoprotein lipase to 8p22 and hepatic lipase to 15q21*, Genomics 1:138–44 [1987]). The gene is near microsatellite marker D8S1715 and flanked by microsatellites D8S261 and D8S280. Closer flanking sequences of human LPL are defined by GENBANK accession numbers M94221 and M94222 (S. Wood et al., *Support for founder effect for two lipoprotein lipase [LPL] gene mutations in French Canadians by analysis of GT microsatellites flanking the LPL gene*, unpublished [1992]). The gene spans about 30 kb and contains 10 exons encoding a 475 amino acid protein including a 27 amino acid secretory signal peptide. (S. Deeb and R. Peng, *Structure of the human lipoprotein lipase gene*, Biochemistry 28(10):4131–35 [1989]; T. G. Kirchgessner et al., *Organization of the human lipoprotein lipase gene and evolution of the lipase gene family*, Proc. Natl. Acad. Sci. USA 86:9647–51 [1989]).

The 3' end of the human lipoprotein lipase gene, for purposes of the present invention, includes nucleotide positions 4801 through 9734 of the Nickerson reference sequence (SEQ ID NO: 25) extending from intron 6 into intron 9. (GENBANK accession No. AF050163). (D. A. Nickerson et al., *DNA sequence diversity in a 9.7-kb region of the human lipoprotein lipase gene*, Nat. Genet. 19:233–40 [1998]). The complete Nickerson reference sequence is given in Table 1 hereinbelow.

The human subpopulation can be any subpopulation of interest based on ethnicity, gender, age, or other identifiable feature distinguishing the subpopulation from the general population.

In accordance with the method "a first number of subjects" in the human subpopulation is a finite number of subjects with a minimum of 10 or more, and preferably with a minimum number of about 20 to about 40 subjects. The first number can be any number of subjects in the subpopulation up to the total number of individuals in the subpopulation, minus one. The "second number of subjects" can be any number of subjects in the subpopulation up to the total number of individuals in the subpopulation. The minimum of the second number of subjects in the human subpopulation is an appropriate number known to the skilled artisan, depending on several factors, including the frequency of particular haplotypes in the subpopulation, the frequency of particular phenotypes of interest in the subpopulation, the strength of association between a haplotype and the phenotype of interest, the desired level of statistical significance, and other like factors.

Gabriel et al. (15) showed that the human genome is organized in haplotype blocks (most of which are longer than 10 kilobases), with three to five commonly occurring (>5%) haplotypes per block. Only six to eight variants were sufficient to define the most common haplotypes in each block. Genotyping six to eight variants thus allows determination of the most frequently occurring haplotypes in a population for association analysis. The availability of family data assists this approach by facilitating unambiguous determination of haplotypes in a more efficient and less expensive manner, based on genotyping at single variants. Variants of interest can also be selected from available databases, particularly but not exclusively, with respect to a group of non-related individuals.

A benefit of a haplotype-based analysis is that it captures all of the variation across a region, which should improve the ability to detect an association.

The "genome" of an individual member of a species comprises that individual's complete set of genes. Particular locations within the genome of a species are referred to as "loci" or "sites". "Alleles" are varying forms of the genomic DNA located at a given site. In the case of a site where there are two distinct alleles in a species, referred to as "A" and "B", each individual member of the species can have one of four possible combinations: AA; AB; BA; and BB. The first allele of each pair is inherited from one parent, and the second, on a matching chromosome, is inherited from the other parent.

The "genotype" of an individual at a specific site, or in a combination or group of associated polymorphic sites (i.e., haplotype), in the individual's genome refers to the specific combination of alleles that the individual has inherited.

The "phenotype" of an individual refers to one or more of these observable physical characteristics. An individual's phenotype is driven in large part by constituent proteins in the individual's proteome, the collection of all proteins produced by the cells comprising the individual and coded for in the individual's genome, but genetic regulatory elements can also produce a phenotype.

For the purpose of the present invention, a "genetic marker" is a single nucleotide polymorphism (SNP). "Variant", "marker", and "polymorphism" are used interchangeably herein.

For purposes of the present invention, detecting, evaluating, or assessing the presence or absence of a genetic marker (i.e., an allele) or heterozygosity or homozygosity of the subject with respect to the marker, is detected in a biological sample collected from the individual that contains the individual's genomic DNA (such as, but not limited to, a blood, saliva, or tissue biopsy sample, which biological sample can be freshly collected or suitably stored to preserve the DNA) by employing suitable biochemical genotyping analytical assay means. Analytical hybridization or polynucleotide sequencing means are typically employed, optionally after amplification of DNA in the biological sample, for example, by using PCR-based amplification means. High throughput analyses can optionally be achieved by multiplexing techniques known in the art. The genotyping analytical assay means can optionally be performed with commonly available robotic apparati and/or very dense array detection apparati. Probes, primers, and protocols useful in genotyping of a biological sample with respect to markers and haplotypes of the LPL gene are described, for example, in Table 2 and the Examples herein, and others are known to the skilled artisan (see, e.g., U.S. Pat. No. 6,297,014).

The present invention relates to a method of detecting a genetic predisposition in a Mexican-American human subject for developing insulin resistance. That a genetic "predisposition" is detected means that the subject, who does not currently exhibit insulin resistance, has a greater than normal risk of developing insulin resistance in the future, compared with the Mexican-American subpopulation as a whole.

Similarly, with respect to the inventive methods of detecting a lower than normal risk in a Mexican-American human subject for developing insulin resistance or coronary artery disease, respectively, "lower than normal" is in comparison with the Mexican-American subpopulation as a whole.

For the purposes of the present invention, a "Mexican-American" is an individual with at least 3 of 4 grandparents native to Mexico. A Mexican-American subpopulation is a human subpopulation (i.e., an ethnic subpopulation of the general human population) consisting of such individuals.

The invention will now be described in greater detail by reference to the following non-limiting examples.

EXAMPLES

Example 1

Lipoprotein Lipase Gene Haplotypes in Mexican-Americans: Structure and Association with Coronary Artery Disease Briefly, six polymorphisms sufficient to distinguish the most common haplotypes in the 3' end of LPL were identified by genotyping ten polymorphisms in a small pilot population. These were used to haplotype LPL in large family samples of Mexican-Americans and non-Hispanic Caucasians. A case-control association study was performed comparing Mexican-Americans with and without coronary artery disease. The two ethnic groups exhibited significant genetic differences. Among Mexican-Americans, homozygosity for LPL haplotype 1 was protective against coronary artery disease (OR=0.50, 95% CI 0.27–0.91). This study outlines the haplotype structure of the LPL gene, illustrates the utility of haplotype-based analysis in association studies, and demonstrates the importance of defining haplotype frequencies for different ethnic groups.

Materials and Methods

Subjects. The UCLA/Cedars-Sinai Mexican-American Coronary Artery Disease (MACAD) Project enrolls families ascertained through a proband with coronary artery disease, determined by evidence of myocardial infarction on electrocardiogram or hospital record, evidence of atherosclerosis on coronary angiography, or history of coronary artery bypass graft or angioplasty. DNA is obtained from all available family members, and the adult offspring of the proband and the spouses of those offspring are also asked to undergo a series of tests to characterize their metabolic and cardiovascular phenotype, including indices of insulin resistance determined by euglycemic clamp study, lipid parameters, lipase activities, and carotid intima-media thickness.

In a separate study, non-Hispanic Caucasian families were recruited for a genetic linkage study to determine the influence of specific genes on inter-individual variation in the lipoprotein response to a low-fat, high-carbohydrate diet. Siblings were placed on either a high-fat or a low-fat diet and changes in lipids and lipoproteins were monitored. We examined this population in terms of haplotype frequency for comparison to Mexican-Americans.

Individuals with at least 3 of 4 grandparents native to Mexico were classified as "Mexican American" in our studies.

Genotyping

An early stage of our haplotyping methodology consists of genotyping a number of single nucleotide polymorphisms (SNPs) spanning a region of a candidate gene in a limited number of subjects. Haplotypes are then constructed using these variants, with subsequent selection of a smaller number of variants that allow discrimination of the most common haplotypes on the majority of chromosomes observed in the population. In the second stage of the haplotyping protocol, the restricted set of SNPs identified in the first stage is genotyped in a large number of individuals using a high-throughput technology and used to determine haplotypes on a population scale.

Twenty-nine subjects from 8 randomly selected families from MACAD were genotyped at 10 single nucleotide polymorphisms (4872, 5168, 5441, 6863, 7315, 8292, 8393, 8852, 9040, 9712) originally delineated in the MDECODE (Molecular Diversity and Epidemiology of Common Disease) project, a study of Finnish, non-Hispanic Caucasian Americans; and African American subjects (9). The numbering of the SNPs corresponds to that reported by Nickerson, et al. (9; see Table 1) and corresponds to GENBANK accession number AF050163 (SEQ ID NO: 25).

TABLE 1

Nickerson reference sequence. (GENBANK accession No. AF050163). (D. A. Nickerson et al., DNA sequence diversity in a 9.7-kb region of the human lipoprotein lipase gene, Nat. Genet. 19:233-40 [1998]). The complete Nickerson reference sequence is the following:

SEQ ID NO:25

```
   1 TGTAACACAA AATTAAAATA AGTAGAATTA GTTTTCAGTA TTTCCTATAT TTGGAAAACA
  61 ATATTTATAT TCATTTTGTT TCTTTTAGTT TTATTTTTGG CAGAACTGTA AGCACCTTCA
 121 TTTTCTTTTT CTTCCAAAGG AGGAGTTTAA CTACCCTCTG GACAATGTCC ATCTCTTGGG
 181 ATACAGCCTT GGAGCCCATG CTGCTGGCAT TGCAGGAAGT CTGACCAATA AGAAAGTCAA
 241 CAGAATTACT GGTAAGAAAG CAATTTCGTT GGTCTTATCA TAAGAGGTGA AAAGACTGTC
 301 ATTCTGAGAG AGAATCAGAA CAAATTTTGT TAAATACCCA CATGTGTGGT GTTCTTCCCG
 361 GAGACATGAC CAGCACTTGA TTATCTCATT GTAGGGCTCT TTATTAGGGA TAAGAAAAAA
 421 CACAGACGCT CTCACTGGCT TACTATCCAC TGGCAATAGC ACAGAAATAA AGCATAATTA
 481 CACACAATGC CTGCAGATTT CTCTGGGAAG CCTGTTTCCT CCCACTCTCA GCTCTGTGTT
 541 TTAGTAGTGT AAATGCACAT CAGTACTAGG ACAAAAGAAG AAGGACCAAT TCCAGAGGCC
 601 ACTTCGAAAG AAGACCGTCA TCTAGGCAAA GGTGTGGCAT ACACACAGAG AGAAAGAACC
 661 CACCACTGTT TATACATCTT CTCGACATAT TCAGAAATAA TCTACAAAAG GAAATCCAGC
 721 CATCCTGAGT GGAAATTGCT GCATAAGGCT AGTTAAGAG ACTCAAATTC ATTTTAGAAG
 781 GAGCCAAGCC TCCTTTTATG TCTCTCTAAG TAAAGATACC ATGACTGTAG AATAGGAGCT
 841 AATAAGAATC TAAATAGCTG CCAGTGCATT CAAATGATGA GCAGTGACAT GCGAATGTCA
 901 TACGAATGGA AATTTACAAA TCTGTGTTCC TGCTTTTTTC CCTTTTAAGG CCTCGATCCA
 961 GCTGGACCTA ACTTTGAGTA TGCAGAAGCC CCGAGTCGTC TTTCTCCTGA TGATGCAGAT
1021 TTTGTAGACG TCTTACACAC ATTCACCAGA GGGTCCCCTG GTCGAAGCAT TGGAATCCAG
1081 AAACCAGTTG GGCATGTTGA CATTTACCCG AATGGAGGTA CTTTTCAGCC AGGATGTAAC
1141 ATTGGAGAAG CTATCCGCGT GATTGCAGAG AGAGGACTTG GAGGTAAATA TTATTTAGAA
1201 GCGAATTAAA TGTGACTCTT ATCCTTAACC CTTATTGACC CAATGTCCTA CTCAGTAGCT
1261 TCAAAGTATG TAGTTTTCAT ATACACATTT GGCCAAATTA TGTTTCTGAA GAATTCTGCA
1321 ATGTTCAGCA TGACCACCTT AGAGCCAGGC AGACAGCCAT TTTATCTTTT ATTTACTATA
1381 CTGTAGGCTA CACTGAGCAG TGCACTTACA GTAGCAAGAG AAAAAGGTGG GATTTTAGAC
1441 AGGAAGACTC CACTGACCTC AATAATGGCA TCATAAAATG CTATCTGGCC ACATGTTGTC
1501 ATACCTTGAA TGTAGCTGCA AAGCCAATGG AAAGATTTTA GATGTTACTG GAACAGAAGA
1561 TGTTAATTAG CATAAATCTT CCAAAATGTT CAGAACATAA TGTTAGCTTA ATGTTTTACT
1621 TTAATAATGT TAGCTTGTGT TAAATTTATG ATTTTTGTTT GTTTGTTTTT TGAGATAGAG
1681 TCTTATTCTA TTGCCCAAGC TGGGGTGCAG TCACACAATC ACAGCGACTT GCAATGTTGC
1741 CCAGGCTGGT CTCAAACTCC TGGCCTCAAG TGATCCTCCT GCCTCAGCCT CCCAAAGTTC
1801 TGGGATTGCA GCTGTGAGCC ACCACGCCCA GTTTACGATT TATTTTTAAG AGCCCCTTGC
1861 ATACTTTATA GACATTGGGA CCTACCTAGG ATATTCTCGT TATTTTTGTG CACGTAATAG
1921 AACTTAGAGC ATATTGTTAC TATTTTCGAT TGTCCTAAAA ACTTACAAGG AATTCATTCT
1981 TATGGCATTG CTGATTATTT CTATGTTCAT TTGATATAAA AGAGTGTTAG TAGGGCAGA
2041 ACCCTCAATT GTACATAATA TCAATGATAA AATACAATTC ATTTAACAAT TACCCTCTTA
2101 AGATGTGGTT TCTAGAAATA CAAATTGTCC CTAACTTACA GTTTCCAAC TTTACAATTG
2161 GGCTGTAACA CCATTTTAAG TTGAGAAGCA CGTGATGGTT TGACTTAAAA CTTTTTGACA
```

TABLE 1-continued

Nickerson reference sequence. (GENBANK accession No. AF050163). (D. A. Nickerson et al., DNA sequence diversity in a 9.7-kb region of the human lipoprotein lipase gene, Nat. Genet. 19:233-40 [1998]). The complete Nickerson reference sequence is the following:

```
2221 TTATGATGGG TTTTGGGGGT ATTAAGTGCA TTTTGACTTA CAGTATTTTT GACTTATGAA
2281 GAATTTATTG TAAGGCAAGG GGCAGGTATA TGTTTCTAGA AGCACCTAGA AGTGTTAGAC
2341 ACTTTCAATG TAAGAGAAGG ATGAGATAAA CAAGGAAATC ACACCTCCAC CTTGGAGGCT
2401 TATTACAGCT TCATAAACAT ACTCATAAAT ATAAGAAGCA CAAAAGTCAA AAATTCCCTG
2461 TGAACTTGCA ACTTTCACTC TCTTGAAGGT GGGTGGGCCG CTACCACCAA GAATATCTCC
2521 TGAAATAGGG CCTACAATCA TAAATGCACA GGACTATATC CTTGGGTGAT TCTACTCTAA
2581 CACCACATCT CACCTATTTT AGACATGCCA AATGAAACAC TCTTTGTGAA TTTCTGCCGA
2641 GATACAATCT TGGTGTCTCT TTTTTACCCA GATGTGGACC AGCTAGTGAA GTGCTCCCAC
2701 GAGCGCTCCA TTCATCTCTT CATCGACTCT CTGTTGAATG AAGAAAATCC AAGTAAGGCC
2761 TACAGGTGCA GTTCCAAGGA AGCCTTTGAG AAAGGGCTCT GCTTGAGTTG TAGAAAGAAC
2821 CGCTGCAACA ATCTGGGCTA TGAGATCAAT AAAGTCAGAG CCAAAAGAAG CAGCAAAATG
2881 TACCTGAAGA CTCGTTCTCA GATGCCCTAC AAAGGTAGGC TGGAGACTGT TGTAAATAAG
2941 GAAACCAAGG AGTCCTATTT CATCATGCTC ACTGCATCAC ATGTACTGAT TCTGTCCATT
3001 GGAACAGAGA TGATGACTGG TGTTACTAAA CCCTGAGCCC TGGTGTTTCT GTTGATAGGG
3061 GGTTGCATTG ATCCATTTGT CTGAGGCTTC TAATTCCCAT TGTCAGCAAG GTCCCAGTGC
3121 TCAGTGTGGG ATTTGCAGCC TTGCTCGCTG CCCTCCCCTG TAAATGTGGC CATTACCATG
3181 GGCTAGGCTA TCAGCACAGA GCTCAGAGCT CATTTGGAAC CATCCACCTC GGGTCAACAA
3241 ACTATAACCC TTGTGCCAAA TCCAGCCTAC TTCCTGCTTT TGTAAATAGT TTTTTTAAAA
3301 CTTTTAAGTT CAGGGGTACG TATGTAGGTT TGCTAAAAAG GTAAACTTGT GACATGGGAG
3361 TTTGTTGTCC AGAATATTCC ATCACCCAGG TATTAAGCTT AGTACCCATT AGTTACTTTT
3421 CCTGAAGCTC TCCCTCCTCC CACCCTCTGG GAGGCCCCAG TGTCTGTTGT TCCCCTCTAT
3481 GTGCTCATGC AAAGTTTTAT TAGGACACAG CCACACACAT TCATTACCAT ATTGTCAAAG
3541 GCTGGTTTCA TGCCACCATA ACAGAGTTGA TAGCCCACAG AGCCTAAAAT ATTTACTCCC
3601 TGGCCCTTTA CAGAATGTTC ACAACTTACA TAAAGGCAAG GACCATCTGT CTTATTTATT
3661 TATTTATTTA ATTTGAGATG AAGTCTAGCT TTCTCCTAGG CTGGAGGAGA GGGGCATGAT
3721 CTTGGCTCAC CACAACCTCT GCCTCCCGGG TTCAAATGAT TCCCCTGCCT CAGCCTCCGG
3781 AGTAGCTGGG ATAACAGGCA TGCACCATCA TGCCCAGCTA ATTTTTGTAT TTTTAGTAGA
3841 GAGGGGGTTT CACCGTGTTG ACCAGGCTGG TCTCGAACTG CTGACCTCAG GTGATCTGCC
3901 CTCCTTGGCC TCATCTGTCT TTTTAAATGC AACTATTCCT GGAAGGCAAG AATATCTCAC
3961 ACCTTCTAAG ATACTGCCAT TTTGCCAGGA GTTTGTTTCA CACTTGAATT TCAAGCTTGG
4021 CCTCTTGTTT AGAGGCAGAC CTAAAGGAAT GGTCGGAAAA TGAGAGAGGA GGTCTTCGGA
4081 TAAATCCGGT GAGAGGGACC AACTTCAGGA AGGGTGGCTT TTGTGGAATC CAGATGGAAA
4141 CCTGAGGGAA GGGATGATAT TAAAGAACAG TGGCCCCAGG TAAAACATAT GGCACCCATG
4201 TGTAAGGTGA TTCTTAGAAT CTGTAGAGGT GTCTTTCGTG TATAGAGGT TGAGGCACCT
4261 GTGCTTCAAG GAAACCTTAA CTCTTCAAAA TCAGGCAATG CGTATGAGGT AAAGAGAGGA
4321 CTGTGGGACC ATAATCTTGA AGACACAGAC AGGCTTCACT CATCCCTGCC TCCTGCACCA
4381 GTGGGTTCAA GGCTCTGTCA GTGTCCCCTA GGGCACCTC ACCACTCCCA GCTTCTTCAG
```

TABLE 1-continued

Nickerson reference sequence. (GENBANK accession No. AF050163). (D. A. Nickerson et al., DNA sequence diversity in a 9.7-kb region of the human lipoprotein lipase gene, Nat. Genet. 19:233-40 [1998]). The complete Nickerson reference sequence is the following:

```
4441  CTCTGGCCTG TCCTGCTGCC TGCAAGGGTT TTGCTTAATT CTCAATTCAA TGTCTCTTCA
4501  TCTTTTAGTA GCTGTGGGGT TTTGTTGTTG TTCTTCTGTT TTTGCTTAGT ATCTGACTAC
4561  TTTTTAATTA TAAAAAGAGA TGTATCTAAA CAAAATAGAG ATTGTTATCA GAAGTTCACA
4621  ACATTTATTA AAAATTTTTT CACCTGGACA AGAGTCTAAA GCAGCATAAA AATATGGTCT
4681  GCTATATTCT AAACCATCAG TCTTAAGAGA TCTGTGTCTC AGCTTAAGAG AAAATACATT
4741  TAATAGACAG TAACACAAAT AAGAAAAAAA TCTGACCAAG GATAGTGGGA TATAGAAGAA
4801  AAAACATTCC AAGAATTATT TTATTTATTT ATTTATTTAT TTATTTATTT ATTTATTTAT
4861  TTTTGAGACA CGGTCTCGCT CAGTTACCCA GGCTGGAGTG CAGCGGCGCA ATCTTAACTC
4921  ACTGCAACCT CTGCTTTCCG GTTCAAGCGA TTCTCCTGCC TCAGCCTCCT GAGTAACTGG
4981  GATTACAGGC ACCCGCCACC ACGCCCAACT AATTTCTGTA TTTTTCTTAG TAGAAACAGG
5041  GTTTCACCAT GTTGGCCAAG CTAGTCTCAA ACTCCTGACC TCAGGTGATT CACCCACCAA
5101  GGCCTCCCAA AGTGCTGGGA TTACAGGCAT GAGCCACCAT GCCTGGCCTC CAAAAACTCT
5161  TTTTTCCTCC ATCATCATGG TTCTATTTTA GTCCTGCTGC CTTTCCTTTT AACCTCTCCC
5221  CAGGCCCATT TGCTCAGGGT TTTTGGTAGA GACCAGAGGA GGGGCAGGGA GGAGATATAG
5281  AAGTTCAACT ACCTGCTTCC AGAGGCTGTC CCTAGTATAG AATACTTTAG GGGCTGGCTT
5341  TACAAGGCAG TCCTTGTGGC CTCACTGATG GCTCAATGAA ATAAGTTCTT TTTTAAAAAA
5401  AATTTTATTT ATTTCCATAG GTTATTGGGG GAACAGGTGG TGTTTGGTTA CATGAGTAAG
5461  TTCTTTAGTA GTGATTTGTG AGATTTTGGT GTGCCCATTA CGGAATGGAA AAATCAACGA
5521  AATAAGTTCT ATGATGCACC TACTAGACAC CTAATCTGCA CTAGATGGTG GGGGAATTAA
5581  GAGCATGGGC ATGATCCTGT GACCGGAAGC CCGCTTACAG TCAGGGTGGA GGACAGACCT
5641  ACTCATGAAA CAAACACAGT GACATATAGT GACACAGAAG CAAATGTCAA ATATGCTTGC
5701  TCCAGATGCT AAGGCACAAG ATGGCCAAGG ATGGCGGAGT TCATGGAGAA AGCATCATGA
5761  GTGTTTTGGC CTTCTGATTT GATCTCCCTA GCACCCCTCA AAGATGGCTA CTTCCTAATG
5821  CTGCTTGGCA ATTCAGACAC ATTTGGGTTT TTCCTATGCA TATAACCACA CTTTTCTGAA
5881  AGGGAGTAGA ATTCAAGGTC TGCATTTTCT AGGTATGAAC ACTGTGCATG ATGAAGTCTT
5941  TCCAAGCCAC ACCAGTGGTT CCATGTGTGT GCACTTCCGG TTTGAGTGCT AGTGAGATAC
6001  TTCTGTGGTT CTGAATTGCC TGACTATTTG GGGTTGTGAT ATTTTCATAA AGATTGATCA
6061  ACATGTTCGA ATTTCCTCCC CAACAGTCTT CCATTACCAA GTAAAGATTC ATTTTTCTGG
6121  GACTGAGAGT GAAACCCATA CCAATCAGGC CTTTGAGATT TCTCTGTATG GCACCGTGGC
6181  CGAGAGTGAG AACATCCCAT TCACTCTGTG AGTAGCACAG GGGGCGGTC ATCATGGCAC
6241  CAGTCCCTCC CCTGCCATAA CCCTTGGTCT GAGCAGCAGA AGCAGAGAGC GATGCCTAGA
6301  AAACAAGTCT TTAGTTAAAA AAATCAGAAT TCAAAATTG AGGTCTTTCC TCTATTTGAT
6361  ATTGAGAAAA AAATGCTTCA AATTGGCCAT TTTATTTTCA CTTACTAGTT ATATTTTTT
6421  ATTTATCATC TTATATCTGT TTATTTCTTT TATAAAGCTG CTGTTAAACA ATATAATTAA
6481  ACTATCTCAA AAGGTTTGAC ATTAAAGAAA ATGAGCAATG GTAACAGGAA ACCACTCTAT
6541  AGATGTACAT ATAATATGTA CAGAAAATAT AAGTAGTAAG AAGTCCATGA CAAAGTGTTA
6601  GCTCTTTTT TTTTTTTTTT TTTTTTTTTT TTTGAGATGG AGTCTCTCTC CTATTGCCCA
```

TABLE 1-continued

Nickerson reference sequence. (GENBANK accession No. AF050163). (D. A. Nickerson et al., DNA sequence diversity in a 9.7-kb region of the human lipoprotein lipase gene, Nat. Genet. 19:233-40 [1998]). The complete Nickerson reference sequence is the following:

```
6661 GGCTGGAGTG CAGTGATTCG ATCTCAGCTC ACTGCAACCT CTACCTCCCG AGTTCAAACA
6721 ATTCTTCTGT CTCAGCCTCC CGAGTAGCTG GGGCTGCAGG TGCCCACCAC CATGCCCAGC
6781 TAATTTTTGT ATTTTTAGTA GCGACAGGGT CTCACCATGT TGGCCAAGCT GGTCTTGAAT
6841 TCCTGATCTC AGGTGATCCA CCCGCCTCGG CCTCCCAAAG TGCTGGGATT ACAGGTGTGA
6901 GCCACCATGC CCAGCCTACC CTTTACTACT AATCAAAGAA ATAAAAGTAA GGCAACTTGA
6961 TACTTTTACA ATTACTAGAT GAACAAATCT TTAAAAATAG CCAGTGCAGA CAAGGTGGTG
7021 AAGCAGAACA TGCGAACCTA CCATGCATCA TTCACGGCTA GAACCCTCCA GGTGCGGAAG
7081 GTAGTATTTT AATAACTTTC CATAGCTACA AAATATTATT ACATAGAAGG GAGTGATTTT
7141 TTTCTAATAT TTATCCTAAA GAAATAGTCA ACAAACATTT TTAAAAAACA TCAATTACAG
7201 TCGTACCTAT ACTAGCATAA ATTAGAAACC CAGTATCCAA CATTGAGGCA GTGGGTAAAT
7261 GAATCGTGGT TTATCAAGTC ATTAAAATCA ATCTAGCCTT TAAAAACTAT AATTGTAGGA
7321 AACCCAGGAA AACATAGTAA AAAATGGAAT ATAAAATCTA AAGAGAATAA AGAATAGAGA
7381 ATCGTATGTG TGCTATGATT GTAGCTAAAT AATGTTCAAG TATCAACACA AATTGAAAAG
7441 GAATACATGA AAATGAAAAT TATATTTCTG AATGATTGAC TTCAGGATTT TCTTTTAGAA
7501 TTGTATTAAA TAGTTCATGT CATTAGGATA AATGCTGGAA TGTGGATATA ATTTAAAATA
7561 TACTAAATGC CATCGACCTT CATTTTGAGT TCTTTGTTGG ACATTTTTGT GCATTTTTAA
7621 AATATCCCCT AAATAATAAA GCTATTTATA TTTGGAGAGG AGAAAAAAAA GTGGGGGGCA
7681 GGGAGAGCTG ATCTCTATAA CTAACCAAAT TTATTGCTTT TTTGTTTAGG CCTGAAGTTT
7741 CCACAAATAA GACATACTCC TTCCTAATTT ACACAGAGGT AGATATTGGA GAACTACTCA
7801 TGTTGAAGCT CAAATGGAAG AGTGATTCAT ACTTTAGCTG GTCAGACTGG TGGAGCAGTC
7861 CCGGCTTCGC CATTCAGAAG ATCAGAGTAA AAGCAGGAGA GACTCAGAAA AAGTAATTAA
7921 ATGTATTTTT CTTCCTTCAC TTTAGACCCC CACCTGATGT CAGGACCTAG GGGCTGTATT
7981 TCAGGGGCCT TCACAATTCA GGGAGAGCTT TAGGAAACCT TGTATTTATT ACTGTATGAT
8041 GTAGATTTTC TTTAGGAGTC TTCTTTTATT TTCTTATTTT TGGGGGGCGG GGGGGGAAGT
8101 GACAGTATTT TTGTATTTCA TGTAAGGAAA ACATAAGCCC TGAATCGCTC ACAGTTATTC
8161 AGTGAGAGCT GGGATTAGAA GTCAGGAATC TCAGCTTCTC ATTTGGCACT GTTTCTTGTA
8221 AGTACAAAAT AGTTAGGGAA CAAACCTCCG AGATGCTACC TGGATAATCA AAGATTCAAA
8281 CCAACCTCTT CAAGAAGGGT GAGATTCCAA GATAATCTCA ACCTGTCTCC GCAGCCCCAC
8341 CCATGTGTAC CCATAAAATG AATTACACAG AGATCGCTAT AGGATTTAAA GCTTTTATAC
8401 TAAATGTGCT GGGATTTTGC AAACTATAGT GTGCTGTTAT TGTTAATTTA AAAAAACTCT
8461 AAGTTAGGAT TGACAAATTA TTTCTCTTTA GTCATTTGCT TGTATCACCA AAGAAGCAAA
8521 CAAACAAACA AAAAAAAAA GAAAAAGATC TTGGGGATGG AAATGTTATA AAGAATCTTT
8581 TTTACACTAG CAATGTCTAG CTGAAGGCAG ATGCCCTAAT TCCTTAATGC AGATGCTAAG
8641 AGATGGCAGA GTTGATCTTT TATCATCTCT TGGTGAAAGC CCAGTAACAT AAGACTGCTC
8701 TAGGCTGTCT GCATGCCTGT CTATCTAAAT TAACTAGCTT GGTTGCTGAA CACCGGGTTA
8761 GGCTCTCAAA TTACCCTCTG ATTCTGATGT GGCCTGAGTG TGACAGTTAA TTATTGGGAA
8821 TATCAAAACA ATTACCCAGC ATGATCATGT ATTATTTAAA CAGTCCTGAC AGAACTGTAC
```

TABLE 1-continued

Nickerson reference sequence. (GENBANK accession No. AF050163). (D. A. Nickerson et al., DNA sequence diversity in a 9.7-kb region of the human lipoprotein lipase gene, Nat. Genet. 19:233-40 [1998]). The complete Nickerson reference sequence is the following:

```
8881 CTTTGTGAAC AGTGCTTTTG ATTGTTCTAC ATGGCATATT CACATCCATT TTCTTCCACA

8941 GGGTGATCTT CTGTTCTAGG GAGAAAGTGT CTCATTTGCA GAAAGGAAAG GCACCTGCGG

9001 TATTTGTGAA ATGCCATGAC AAGTCTCTGA ATAAGAAGTC AGGCTGGTGA GCATTCTGGG

9061 CTAAAGCTGA CTGGGCATCC TGAGCTTGCA CCCTAAGGGA GGCAGCTTCA TGCATTCCTC

9121 TTCACCCCAT CACCAGCAGC TTGCCCTGAC TCATGTGATC AAAGCATTCA ATCAGTCTTT

9181 CTTAGTCCTT CTGCATATGT ATCAAATGGG TCTGTTGCTT TATGCAATAC TTCCTCTTTT

9241 TTTCTTTCTC CTCTTGTTTC TCCCAGCCCG GACCTTCAAC CCAGGCACAC ATTTTAGGTT

9301 TTATTTTACT CCTTGAACTA CCCCTGAATC TTCACTTCTC CTTTTTTCTC TACTGCGTCT

9361 CTGCTGACTT TGCAGATGCC ATCTGCAGAG CATGTAACAC AAGTTTAGTA GTTCCCGTTC

9421 TGGCTGTGGG TGCAGCTCTT CCCAGGATGT ATTCAGGGAA GTAAAAAGAT CTCACTGCAT

9481 CACCTGCAGC CACATAGTTC TTGATTCTCC AAGTGCCAGC ATACTCCGGG ACACACAGCC

9541 AACAGGGCTG CCCCAAGCAC CCATCTCAAA ACCCTCAAAG CTGCCAAGCA AACAGAATGA

9601 GAGTTATAGG AAACTGTTCT CTCTTCTATC TCCAAACAAC TCTGTGCCTC TTTCCTACCT

9661 GACCTTTAGG GCTAATCCAT GTGGCAGCTG TTAGCTGCAT CTTTCCAGAG CGTCAGTACT

9721 GAGAGGACAC TAAG//
```

8393 is the HindIII variant and 9040 is the Ser447Stop variant. 4872, 5168, and 5441 are in intron 6; 6863 and 7315 are in intron 7; 8292 and 8852 are in intron 8; 9712 is in intron 9; these markers were selected because they spanned a region of the LPL gene downstream of a recombination hotspot and had a minor allele frequency of 15% or greater in MDECODE 12 PCR amplification followed by restriction digest with HindIII was used to genotype the polymorphism at 8393. A single nucleotide primer extension method was used to genotype the remaining nine SNPs (4872, 5168, 5441, 6863, 7315, 8292, 8852, 9040, 9712). Analysis of these initial data showed that a restricted set of six SNPs encompassed all the major 3' end haplotypes.

Large-scale genotyping of these six SNPs in 514 subjects from 85 MACAD families and 629 subjects from 157 non-Hispanic Caucasian families was performed using the 5'-exonuclease (Taqman™ MGB) assay (10). PCR primer and oligonucleotide probe sequences are listed in Table 2 below.

TABLE 2

Primers and probe sequences used in 5'-exonuclease assay.

| Variant | PCR primers | | Taqman MGB probes | |
|---|---|---|---|---|
| 7315 | Forward<br>5'-TCAAGTCATTAAAATCAATCTAGCCTTT-3'// | SEQ ID NO:1; | 5'-CCTGGGTTTCCTAcAAT-3'//<br>5'-CCTGGGTTTCCTAgAAT-3'// | SEQ ID NG:13;<br>SEQ ID NO:14 |
| | Reverse<br>5'-TTCTCTTTAGATTTTATATTCCATTTTTTACTATG-3'// | SEQ ID NO:2 | | |
| 8292 | Forward<br>5'-CCTGGATAATCAAAGATTCAAACCA-3'// | SEQ ID NO:3; | 5'-CTCACCCTTCTtGAAGA-3'//<br>5'-TCACCCTTCTgGAAGA-3'// | SEQ ID NO:15;<br>SEQ ID NO:16 |
| | Reverse<br>5'-GGAGACAGGTTGAGATTATCTTGGA-3'// | SEQ ID NO:4 | | |
| 8393 | Forward<br>5'-CATAAAATGAATTACACAGAGATCGCTAT-3'// | SEQ ID NO:5; | 5'-CACATTTAGTATAAAaGC-3'//<br>5'-CACATTTAGTATAAAcGC-3'// | SEQ ID NO:17;<br>SEQ ID NO:18 |
| | Reverse<br>5'-TCAATCCTAACTTAGAGTTTTTTTAAATTAACA-3'// | SEQ ID NO:6 | | |

TABLE 2-continued

Primers and probe sequences used in 5'-exonuclease assay.

| Variant | PCR primers | | Taqman MGB probes | |
|---|---|---|---|---|
| 8852 | Forward<br>5'-GTGGCCTGAGTGTACAGTTAATT-3'// | SEQ ID NO:7; | 5'AGCATGATCATGTAtTAT-3'//<br>5'-CAGCATGATCATGTAgTAT-3'// | SEQ ID NO:19;<br>SEQ ID NO:20 |
|  | Reverse<br>5'-ATCAAAAGCACTGTTCACAAAGGTA-3'// | SEQ ID NO:8 |  |  |
| 9040 | Forward<br>5'TTGTGAAATGCCATGACAAGTCT-3'// | SEQ ID NO:9; | 5'-CCAGCCTgACTTC-3'//<br>5'-ACCAGCCTcACTTC-3'// | SEQ ID NO:21;<br>SEQ ID NO:22 |
|  | Reverse<br>5'-CCAGTCAGCTTTAGCCCAGAA-3'// | SEQ ID NO:10 |  |  |
| 9712 | Forward<br>5'-TCCATGTGGCAGCTGTTAGC-3'// | SEQ ID NO:11; | 5'-CCAGAGCgTCAGTAC-3'//<br>5'-CCAGAGCaTCAGTAC-3'// | SEQ ID NO:23;<br>SEQ ID NO:24 |
|  | Reverse<br>5'-GAGTAGTGAAGGTCACATGCTTAGTGT-3'// | SEQ ID NO:12 |  |  |

In this assay, allele-specific oligonucleotide probes are labeled with different fluorophores (FAM or VIC) at their 5'-ends and with a quencher molecule at the 3'-end. The quencher interacts with the fluorophores by fluorescence resonance energy transfer, quenching their fluorescence. These probes are included in the PCR reaction mixture amplifying a 100–150 base pair segment with the polymorphism at the center. During annealing, the probes hybridize to the PCR products, and during extension, the 5'-3' exonuclease activity of the DNA polymerase degrades perfectly matched annealed probes, separating the fluorophore from the quencher. Imperfectly matched probes are displaced into solution without degradation. Comparison of relative fluorescence from each fluorophore allows determination of genotype.

Data Analysis. Based on pedigree structures and genotype data of all individuals in each pedigree, haplotypes were reconstructed as the most likely set (determined by the maximum likelihood method) of fully-determined parental haplotypes of the marker loci for each individual in the pedigree, using the simulated annealing algorithm implemented in the program Simwalk2. (19) All comparisons between groups of subjects comprised comparisons of unrelated founders, and only founder chromosome data are presented in the tables. Founder haplotypes, i.e. those haplotypes from parents and individuals marrying into the family, were used to calculate haplotype frequencies in 482 chromosomes from 241 Mexican-American founders and in 582 chromosomes from 291 non-Hispanic Caucasian founders. Six Mexican-American and 21 non-Hispanic Caucasian founders were excluded from analysis because their haplotypes could not be unambiguously determined. The $\chi^2$ test was used to compare allele and haplotype frequencies between the Mexican-Americans without coronary artery disease and the non-Hispanic Caucasians.

A case-control association study of coronary artery disease was performed by comparing haplotype frequencies between Mexican-American founders with and those without coronary artery disease. The cases were 77 probands (154 chromosomes) with coronary artery disease; the controls (164 individuals, 328 chromosomes) were their spouses plus the spouses marrying into the offspring generation. Because the cases and controls were genetically unrelated, their allele and haplotype frequencies and gender distribution were compared using the $\chi^2$ test. Student's T test was used to compare the mean age of the cases versus the controls. Odds ratios for coronary artery disease by haplogenotype were calculated, using logistic regression analysis to adjust for any confounding effects of age or sex in the case-control comparison. Analyses were performed using SAS System software (20).

Results

In a pilot study, the haplotypes of 28 unique chromosomes were derived using Mexican-American family data and are shown in Table 3 (below) in order of frequency. These results were used to select the markers genotyped in the large population samples. As seen in Table 3, markers 7315, 8292, 8393, 8852, and 9040 are sufficient to distinguish the haplotypes from each other. In addition to these five SNPs, 9712 was also chosen because it is predicted to distinguish two major ancient clades according to the haplotype tree constructed by Templeton, et al. (6) in the Molecular Diversity and Epidemiology of Common Disease (MDECODE) project. The results reported herein are consistent with their study of the haplotype structure of 9.7 kb of the LPL gene that described four ancient cladistic groups. Markers 7315, 8393, and 9712 are useful to distinguish all four of the ancient 3' LPL clades.

TABLE 3

Pilot study LPL haplotypes.

| Haplotype | 4872 | 5168 | 5441 | 6863 | 7315 | 8292 | 8393H | 8852 | 9040 | 9712 | Count | Frequency |
|---|---|---|---|---|---|---|---|---|---|---|---|---|
| 1 | A | T | T | C | G | A | T | T | C | G | 13 | 46.4% |
| 2 | G | C | T | C | G | A | G | G | G | G | 4 | 14.3% |
| 3 | A | T | T | C | G | A | G | G | C | A | 3 | 10.7% |

TABLE 3-continued

Pilot study LPL haplotypes.

| Haplotype | 4872 | 5168 | 5441 | 6863 | 7315 | 8292 | 8393H | 8852 | 9040 | 9712 | Count | Frequency |
|---|---|---|---|---|---|---|---|---|---|---|---|---|
| 4 | A | T | T | C | G | C | T | T | C | G | 3 | 10.7% |
| 5 | G | C | T | T | C | A | G | G | C | A | 3 | 10.7% |
| 6 | G | T | T | C | C | A | T | T | C | G | 1 | 3.6% |
| 7 | A | T | T | C | G | A | T | G | C | G | 1 | 3.6% |

In the second stage, the six selected markers were then genotyped in 514 Mexican-American subjects from 85 families and 629 subjects from 157 non-Hispanic Caucasian families. The allele frequencies are shown in Table 4 (below). The markers from Mexican-Americans without coronary artery disease are presented in Table 4 in order to eliminate any disease-based ascertainment bias in delineating the ethnic comparison.

TABLE 4

LPL SNP allele frequencies in Mexican-Americans and non-Hispanic Caucasians.

| Position | Variant | Mexican-American without CAD (328 chromosomes) | Non-Hispanic Caucasian (582 chromosomes) | P value |
|---|---|---|---|---|
| 7315 | G → C | 0.89 | 0.85 | 0.08 |
| 8292 | A → C | 0.85 | 0.79 | 0.03 |
| 8393 | T → G | 0.80 | 0.71 | 0.003 |
| 8852 | T → G | 0.78 | 0.70 | 0.01 |
| 9040 | C → G | 0.93 | 0.90 | 0.10 |
| 9712 | G → A | 0.88 | 0.81 | 0.02 |

Of note, while 9040 (Ser447Stop) was extremely rare in the previous MDECODE study subjects (not detected in African Americans or Finns and found with a frequency of 4% in U.S. non-Hispanic Caucasians), in this study it was found with a frequency of 7% in Mexican Americans and 9% in our non-Hispanic Caucasians. Comparing Mexicanan-Americans to non-Hispanic Caucasians, the allele frequencies were significantly different for four out of the six variants (Table 4).

The founder haplotype frequencies from the Mexican-Americans without coronary artery disease (as determined by EKG or by hospital records of, e.g., angioplasty, coronary artery bypass graft surgery, or angiography) were compared with those of the non-Hispanic Caucasians. The six most common haplotypes, comprising over 99% of the observed haplotypes for each group, are presented in Table 5 (below). Both groups shared haplotype 1 as the most common haplotype. There were several differences between the two groups in regards to the other haplotypes. Haplotypes 2, 3, 4, and 5 were more common in the non-Hispanic Caucasian population; haplotypes 1 and 6 were more common in the Mexican-Americans. These differences reached statistical significance for the three most frequent haplotypes.

In the case-control study, Mexican-American probands with coronary artery disease were compared with their spouses and the spouses of their offspring, none of whom had coronary artery disease. Thus, these case and control individuals were all genetically unrelated. The mean age of the cases was 62.2 years; that of the controls was 42.6 years (P<0.0001). This age difference was expected, given that the control group was comprised of individuals from both the parental and offspring generations. The sex distribution was similar between the groups, with males comprising 44% of the cases and 38% of the controls ($\chi^2=0.9$, P=0.35).

TABLE 5

LPL haplotype frequencies in Mexican-Americans compared to non-Hispanic Caucasians.

| Haplotype | 7315 | 8292 | 8393 | 8852 | 9040 | 9712 | Mexican | Freq | Caucasian | Freq | P value |
|---|---|---|---|---|---|---|---|---|---|---|---|
| 1. | G | A | T | T | C | G | 206 | 62.8% | 284 | 48.8% | <0.0001 |
| 2. | G | C | T | T | C | G | 50 | 15.2% | 123 | 21.1% | 0.03 |
| 3. | C | A | G | G | C | A | 33 | 10.1% | 85 | 14.6% | 0.05 |
| 4. | G | A | G | G | G | G | 22 | 6.7% | 58 | 10.0% | 0.10 |
| 5. | G | A | G | G | C | A | 8 | 2.4% | 24 | 4.1% | 0.19 |
| 6. | G | A | T | G | C | G | 6 | 1.8% | 5 | 0.9% | 0.20 |
| | | | | | | | 325 | 99.1% | 579 | 99.5% | |

The genotype frequencies for all six markers were in Hardy-Weinberg equilibrium for both the cases and the controls. Allele frequencies of the six SNPs did not differ significantly among the Mexican-Americans according to coronary artery disease status (Table 6). A comparison of genotype frequencies showed no differences between cases and controls, except for a modestly significant difference for the 8393 (HindIII) variant (P=0.05). However, comparison of the common haplotype frequencies between the Mexican-Americans with and without coronary artery disease revealed a significant decrease in the frequency of the most common haplotype in those with disease (Table 7 below). This implies an increase in frequency of less common haplotypes among cases, the detection of which was hindered by the available sample size. Haplotype 1 was associated with a significantly decreased risk of coronary artery disease (P=0.03). Of the less common haplotypes, haplotype 4 was most prominently associated with the greatest risk of coronary artery disease (P=0.10), though this result did not attain statistical significance with the given sample size. A comparison of subjects homozygous for haplotype 1 with subjects with all other genotypes is presented in Table 8 (below). Homozygosity for haplotype 1 was associated with protection against coronary artery disease with an odds ratio of 0.50 (95% CI 0.27–0.91). Use of the logistic regression model to adjust for age and sex, separately and in combination (Table 7), did not alter the significance of this association (odds ratio estimates from 0.39 to 0.51). None of the haplotypes other than haplotype 1 showed a statistically significant association with coronary artery disease (data not shown).

In comparing two different ethnic groups, we found several differences in the allele and haplotype frequencies observed in the 3' LPL markers. Such differences may affect results of association studies conducted in different populations. In particular, different alleles of HindIII occurred at different frequencies, which may account for disparate results of association studies conducted in different populations. For example, a study of postmenopausal Caucasian women found no association of the HindIII variant with glucose or insulin levels, while a study in Chinese men with coronary heart disease found an association of HindIII with steady state plasma glucose levels, a marker of insulin resistance (3,8).

The haplotypes described here can be very useful in future studies exploring the association of the LPL gene with components of the cardiovascular dysmetabolic syndrome.

TABLE 6

LPL SNP allele and genotype frequencies in Mexican-Americans with and without CAD.

| SNP | | Frequency of major allele | P value[a] | Major allele[b] homozygote | Heterozygote | Minor allele[b] homozygote | P value[c] |
|---|---|---|---|---|---|---|---|
| 7315 | Cases | 0.89 | 0.46 | 57 | 20 | 0 | 0.31 |
|  | Controls | 0.87 |  | 131 | 31 | 2 |  |
| 8292 | Cases | 0.85 | 0.41 | 52 | 22 | 3 | 0.48 |
|  | Controls | 0.82 |  | 118 | 42 | 4 |  |
| 8393 | Cases | 0.80 | 0.06 | 39 | 33 | 5 | 0.05 |
|  | Controls | 0.72 |  | 105 | 52 | 7 |  |
| 8852 | Cases | 0.78 | 0.08 | 38 | 33 | 6 | 0.09 |
|  | Controls | 0.71 |  | 100 | 56 | 8 |  |
| 9040 | Cases | 0.93 | 0.10 | 61 | 15 | 1 | 0.14 |
|  | Controls | 0.89 |  | 142 | 22 | 0 |  |
| 9712 | Cases | 0.88 | 0.27 | 54 | 21 | 2 | 0.37 |
|  | Controls | 0.84 |  | 124 | 39 | 1 |  |

[a]For the comparison of allele frequency between cases and controls: $\chi^2$ (1 d.f.)
[b]Major and minor alleles are listed in Table 4.
[c]Major allele homozygotes versus heterozygotes plus minor allele homozygotes, comparing cases and controls: $\chi^2$ (1 d.f.)

TABLE 7

LPL haplotype frequencies in Mexican-Americans with and without coronary artery disease.

| Haplotype | 7315 | 8292 | 8393 | 8852 | 9040 | 9712 | CAD | Freq | No CAD | Freq | P value |
|---|---|---|---|---|---|---|---|---|---|---|---|
| 1. | G | A | T | T | C | G | 81 | 52.6% | 206 | 62.8% | 0.03 |
| 2. | G | C | T | T | C | G | 28 | 18.2% | 50 | 15.2% | 0.42 |
| 3. | C | A | G | G | C | A | 20 | 13.0% | 33 | 10.1% | 0.34 |
| 4. | G | A | G | G | G | G | 17 | 11.0% | 22 | 6.7% | 0.10 |
| 5. | G | A | G | G | C | A | 5 | 3.3% | 8 | 2.4% | 0.61 |
| 6. | G | A | T | G | C | G | 2 | 1.3% | 6 | 1.8% | 0.67 |
|  |  |  |  |  |  |  | 153 | 99.4% | 325 | 99.1% |  |

TABLE 8

Logistic regression analysis comparing haplotype 1 homozygotes with all other haplogenotypes.

| Adjustment | Odds Ratio | 95% CI | P value |
|---|---|---|---|
| None | 0.50 | 0.27–0.91 | 0.02 |
| Sex | 0.51 | 0.28–0.93 | 0.03 |
| Age | 0.41 | 0.18–0.93 | 0.03 |
| Sex and Age | 0.39 | 0.17–0.89 | 0.03 |

This is illustrated here, in that haplotype frequencies were different according to coronary artery disease status. Only one out of six single polymorphic sites was associated with coronary artery disease. This demonstrates that the common approach of examining one or two polymorphisms per candidate gene may fail to detect phenotypic associations. Compared to single-variant analysis, haplotype-based analysis reduces the potential for false negatives in association studies. The benefit of a haplotype-based analysis is that it captures all of the variation across a region, which should, as it did in our study, improve the ability to detect an association. This study thus demonstrates the improved power of haplotyping in eludicating disease gene associations and the importance of ethnic specific haplotype data.

Example 2

Haplotype Analysis of the Association of the Lipoprotein Lipase Gene with Insulin Sensitivity Lipoprotein lipase (LPL) is a candidate gene implicated in features of the cardiovascular dysmetabolic syndrome, atherosclerosis and components of the insulin-resistance syndrome, i.e., hypertension, lipid levels, and fasting insulin.

The aim of this study was to evaluate the relationship between the LPL gene and direct, measurement of insulin sensitivity in Mexican American families ascertained through patients with CAD, a population and disorder with a high frequency of insulin resistance. Insulin senstivity was evaluated by assessment of the glucose infusion rate (GINF) during a euglycemic hyperinsulinemic clamp study, which is widely regarded as the most direct physiologic measurement of insulin sensitivity (38, 39).

Mexican-American nuclear families were ascertained via a parent with documented CAD in the Los Angeles area. A total of 91 adult offspring underwent euglycemic clamp to determine peripheral glucose disposal. Insulin sensitivity ($S_I$) was calculated from the glucose infusion rate (GINF) and increment in plasma insulin over basal for each offspring. Both parents and offspring were genotyped for eight polymorphic markers spanning a distance of 6.9 cM at or near the LPL gene on chromosome 8 (D8S261, LPL3, HindIII, PvuII, LPL5, D8S258, D8S282, D8S136).

Linkage analysis was conducted using linear regression method as implemented in the SIBPAL program of the SAGE package. Association between HindIII polymorphic markers and $S_I$ was evaluated by comparing the maximum likelihood of the two models incorporating familial correlation (with or without the marker) as implemented in the ASSOC program.

Results: Multiple markers at or near the LPL gene showed significant evidence of linkage (0.003p0.05) to $S_I$. Furthermore, a significant association between allele 2 of HindIII polymorphism within the LPL gene itself and insulin sensitivity ($S_I$) was also observed (p=0.008).

This shows a linkage of markers near and within LPL to insulin resistance in a family study of Mexican-Americans ascertained by probands with coronary artery disease, and also shows association of the HindIII polymorphism with a direct measurement of insulin sensitivity ($S_I$, calculated from euglycemic clamp study). HindIII allele 2 is associated with decreased $S_I$. Thus, in Mexican American families ascertained through CAD probands, we have for the first time shown that the LPL gene is both linked and associated with a direct measure of insulin resistance. This observation provides the most direct evidence as to the importance of the LPL gene in the insulin resistance syndrome and provides a pathophysiologic mechanism for its relation to the development of CAD.

In a further study described hereinbelow our goal was to identify specific haplotypes (groups of alleles on the same chromosome) associated with insulin sensitivity in an expanded family sample undergoing glucose clamps.

Example 3

Evidence of Linkage and Association Between LPL and Insulin Sensitivity/Resistance in Mexican-American Hypertension Families We have shown hereinabove that blood pressure (BP) and insulin sensitivity/resistance (IR) cosegregate in Mexican-American families and that there most likely are gene(s) contributing to both BP and IR. Previous studies have shown evidence of linkage and/or association of the HindIII polymorphism in the LPL gene with IR, as well as IR-associated hypertension, dyslipidemia, and atherosclerosis. However, in most cases insulin sensitivity was assessed by indirect methods. To further examine the role of the LPL gene in IR, we genotyped six (7315, 8292, 8393, 8852, 9040, 9712) LPL 3' end single nucleotide polymorphisms (SNPs) in 390 members of 77 Hispanic families ascertained via hypertensive probands. Insulin sensitivity/resistance was directly assessed via hyperinsulinemic euglycemic glucose clamps. Multipoint linkage analyses were performed using SIB-PAL2. Association between the six SNPs, LPL haplotypes and IR-related traits were evaluated using the QTDT program.

Materials and Methods

Subjects. The UCLA/Cedars-Sinai Mexican-American Coronary Artery Disease (MACAD) Project enrolls families ascertained through a proband with coronary artery disease, determined by evidence of myocardial infarction on electrocardiogram or hospital record, evidence of atherosclerosis on coronary angiography, or history of coronary artery bypass graft or angioplasty (30). DNA was obtained from all available family members, and the adult offspring (age 18 or older) of the proband and the spouses of those offspring were also asked to undergo a series of tests to characterize their metabolic and cardiovascular phenotype.

Genotyping. In a study described hereinabove, we determined a set of six SNPs that are sufficient to identify the most common haplotypes occurring in the 3' end of the LPL gene (30). These are 7315, 8292, 8393, 8852, 9040, and 9712. The numbering of the SNPs corresponds to GEN-BANK accession number AF050163, which describes a 9.7 kb segment of the LPL gene originally sequenced in the Molecular Diversity and Epidemiology of Common Disease (MDECODE) project, a study of Finns, non-Hispanic Caucasian Americans, and African-American subjects (9). 8393 is the HindIII variant located in intron 8 and 9040 is the Ser447Stop variant located in exon 9. 7315 is in intron 7; 8292 and 8852 are in intron 8; 9712 is in intron 9.

Large-scale genotyping of the six SNPs in MACAD families was performed using the 5'-exonuclease (Taqman™ MGB) assay (10). PCR primer and oligonucleotide probe sequences are listed in Table 2 (Goodarzi et al.; 30). In this assay, allele-specific oligonucleotide probes were labeled with different fluorophores (FAM or VIC) at their 5'-ends and with a quencher molecule at the 3'-end. The quencher interacts with the fluorophores by fluorescence resonance energy transfer, quenching their fluorescence. These probes are included in the PCR reaction mixture amplifying a 100–150 base pair segment with the polymorphism at the center. During annealing, the probes hybridize to the PCR products, and during extension, the 5'-3' exonuclease activity of the DNA polymerase degrades perfectly matched annealed probes, separating the fluorophore from the quencher. Imperfectly matched probes are displaced into solution without degradation. Comparison of relative fluorescence from each fluorophore allows determination of genotype.

LPL markers were genotyped in 514 individuals from 85 MACAD families. Of these, 29 individual genotypes were discarded because their genotypes were incompatible with their family pedigree, as detected by the program Pedcheck (40). This left 485 individuals genotyped at LPL. The genotype frequencies for all six markers were in Hardy-Weinberg equilibrium.

Phenotyping. The adult offspring of the proband and the spouses of the offspring underwent a three-day phenotyping protocol, which includes indices of insulin resistance determined by euglycemic clamp study, lipid parameters, and carotid intima-media thickness. Of the 485 subjects genotyped at LPL, 125 were from the parental generation that does not undergo phenotyping, and 69 from the offspring generation were not clamped. Thus, 291 subjects from 74 families were both clamped and genotyped for the LPL markers.

Several indices of insulin sensitivity are obtained in the MACAD study. Fasting insulin and glucose, themselves simple surrogate measures of insulin sensitivity, allow calculation of the homeostasis model assessment index (HOMA). Using glucose in mmol/L and insulin in µIU/mL, the HOMA index is (glucose×insulin)/22.5. An ideal, normal-weight person aged <35 years has a HOMA of 1 (41).

During the hyperinsulinemic euglycemic clamp (38), human insulin (Novolin, Clayton, NC; 60 mU/m$^2$/min) was infused for 120 minutes at a constant rate to achieve a plasma insulin concentration of 100 µIU/mL or greater. Blood was sampled every 5 minutes, and the rate of 20% dextrose co-infused was adjusted to maintain plasma glucose concentrations at 95 to 100 mg/dL. The glucose infusion rate (GINF, given in mg/min) over the last 30 minutes of steady-state insulin and glucose concentrations reflects glucose uptake by all tissues of the body (primarily insulin-mediated glucose uptake in muscle) and is therefore a direct physiologic measurement of tissue insulin sensitivity. GINF is also often reported divided by body weight, resulting in a trait termed the M value (mg/kg/min; 38).

Data Analysis. Based on the pedigree structures and genotype data of all individuals in each pedigree, haplotypes were reconstructed as the most likely set (determined by the maximum likelihood method) of fully-determined parental haplotypes of the marker loci for each individual in the pedigree, using the simulated annealing algorithm implemented in the program Simwalk2 (19). Using this method we were able to assign haplotypes to 475 of the 485 genotyped subjects, including 285 of the 291 genotyped and clamped subjects. Founder haplotypes, i.e. those haplotypes from parents and individuals marrying into the families, were used to calculate haplotype frequencies in 482 chromosomes from 241 Mexican-American founders (125 parents, 116 spouses of offspring). The frequencies of the most common haplotypes among 328 chromosomes of the 164 founders (48 parents, 116 spouses) without coronary artery disease are displayed in Table 9 along with the major allele frequencies of the six SNPs. The markers from Mexican-Americans without coronary artery disease are presented in Table 9 in order to eliminate any disease-based ascertainment bias.

TABLE 9

LPL single marker and haplotype frequencies in Mexican-Americans.

| SNPs and major allele frequencies: | 7315 G→C 0.89 | 8292 A→C 0.85 | 8393 T→G 0.80 | 8852 T→G 0.78 | 9040 C→G 0.93 | 9712 G→A 0.88 | Subjects | Freq |
|---|---|---|---|---|---|---|---|---|
| Haplotype 1 | G | A | T | T | C | G | 206 | 62.8% |
| Haplotype 2 | G | C | T | T | C | G | 50 | 15.2% |
| Haplotype 3 | C | A | G | G | C | A | 33 | 10.1% |

TABLE 9-continued

LPL single marker and haplotype frequencies in Mexican-Americans.

| SNPs and major allele frequencies: | 7315 G→C 0.89 | 8292 A→C 0.85 | 8393 T→G 0.80 | 8852 T→G 0.78 | 9040 C→G 0.93 | 9712 G→A 0.88 | Subjects | Freq |
|---|---|---|---|---|---|---|---|---|
| Haplotype 4 | G | A | G | G | G | G | 22 | 6.7% |
| Haplotype 5 | G | A | G | G | C | A | 8 | 2.4% |
| Haplotype 6 | G | A | T | G | C | G | 6 | 1.8% |

Log-transformed (anthropometric measurements, fasting glucose, fasting insulin) or square-root-transformed (HOMA, GINF, M) trait values were used to reduce skewness for all statistical analyses. Unpaired, two-sided T tests were used to compare trait values between men and women.

Linkage was assessed using sib pair analysis (42). The basic idea of this approach is that if a locus influences the quantitative trait or phenotype under study, then siblings that share more alleles at that locus will be more similar in phenotype than siblings that share fewer alleles. Conceptually, this procedure first plots the square of the difference in the quantitative trait between each sibpair versus the number of alleles shared, and then uses linear regression to estimate how much of the difference in the trait depends on the number of alleles shared. A significant linkage is shown by a negative regression coefficient. If there is no linkage, the regression coefficient is expected to be zero. We used the SIBPAL2 program in SAGE 4.2 (43) to implement a sib pair analysis that uses the mean-corrected cross-product instead of the squared difference of the sibs trait values as the dependent variable; this revised method has more power and accommodates multiple sibs in a family (44).

Association was evaluated by quantitative transmission disequilibrium testing for both individual polymorphisms and haplotypes using the QTDT program (45). The transmission disequilibrium test was first developed for dichotomous traits in which alleles transmitted and not transmitted from the parents to affected offspring are compared to determine whether one allele is associated with the disease in question (46). This was later extended to quantitative traits (47). Abecasis, developed a general approach for scoring allelic transmission that accommodates families of any size and uses all available genotypic information (45). Family data allows for the construction of an expected genotype for every non-founder, and orthogonal deviates from this expectation are a measure of allelic transmission. The QTDT program implements this general transmission disequilibrium testing using the orthogonal model of Abecasis (48). Age, gender, and body mass index were specified as covariates. Environmental variance, polygenic variance, and additive major locus were specified in the variance model. In all cases of a positive association result, the population stratification model was also executed to confirm the absence of significant population stratification.

Results

The clinical characteristics of the 291 subjects (112 men, 179 women) who had quantitative assessment of insulin resistance are shown in Table 10 below. This is an adult group of Mexican-Americans of mean age 35.3 years. On average, these individuals are overweight. This may account for the degree of insulin resistance observed; however, it is known that Mexican-Americans have a predisposition to visceral adiposity, hyperinsulinemia, and insulin resistance (49, 50). The mean HOMA level suggests that these people are on average almost four times more insulin resistant than normal. The men had statistically significant higher weight (P<0.0001) and fasting glucose (P=0.0023) levels, while the women had significantly lower GINF (P=0.0001) but not M values.

TABLE 10

Clinical characteristics of 291 genotyped and clamped individuals.

| | Mean | SD | Range |
|---|---|---|---|
| Age (yr) | | | |
| Men (n = 112) | 35 | 9.4 | 19–60 |
| Women (n = 179) | 35.5 | 8.2 | 18–58 |
| Weight (kg)* | | | |
| Men | 84.2 | 15.6 | 52.5–126.6 |
| Women | 72.1 | 14.0 | 38.6–128.5 |
| Body mass index (kg/m$^2$) | | | |
| Men | 28.9 | 4.8 | 17.8–45.4 |
| Women | 29.1 | 5.5 | 18.1–54.8 |
| Fasting glucose (mg/dL)* | | | |
| Men | 96.1 | 9.8 | 74.0–118.0 |
| Women | 92.5 | 9.4 | 56.0–117.0 |
| Fasting insulin (μIU/mL) | | | |
| Men | 15.4 | 8.9 | 5.0–62.0 |
| Women | 15.5 | 7.5 | 2.0–49.0 |
| HOMA (μIU/mL × mmol/L) | | | |
| Men | 3.7 | 2.4 | 1.2–15.9 |
| Women | 3.6 | 1.9 | 0.5–14.0 |
| GINF (mg/min)* | | | |
| Men | 428.6 | 196.8 | 105.9–1031.5 |
| Women | 343.5 | 147.5 | 20.7–1010.5 |
| M (mg/kg/min) | | | |
| Men | 5.4 | 2.8 | 1.0–13.9 |
| Women | 5.0 | 2.4 | 0.2–14.9 |

*P < 0.005 comparing men versus women

Linkage results are shown in Table 11. Of the several indices of insulin sensitivity, linkage was demonstrated only for the direct quantification represented by GINF. The M value, a clamp-derived index equal to GINF/body weight, was not significantly linked to LPL haplotypes.

TABLE 11

Linkage results for measurements of insulin sensitivity and LPL haplotypes

| Phenotype | P value (from SIBPAL) |
|---|---|
| Fasting glucose | 0.57 |
| Fasting insulin | 0.44 |
| HOMA | 0.34 |
| GINF | 0.034 |
| M | 0.32 |

Figure 2:
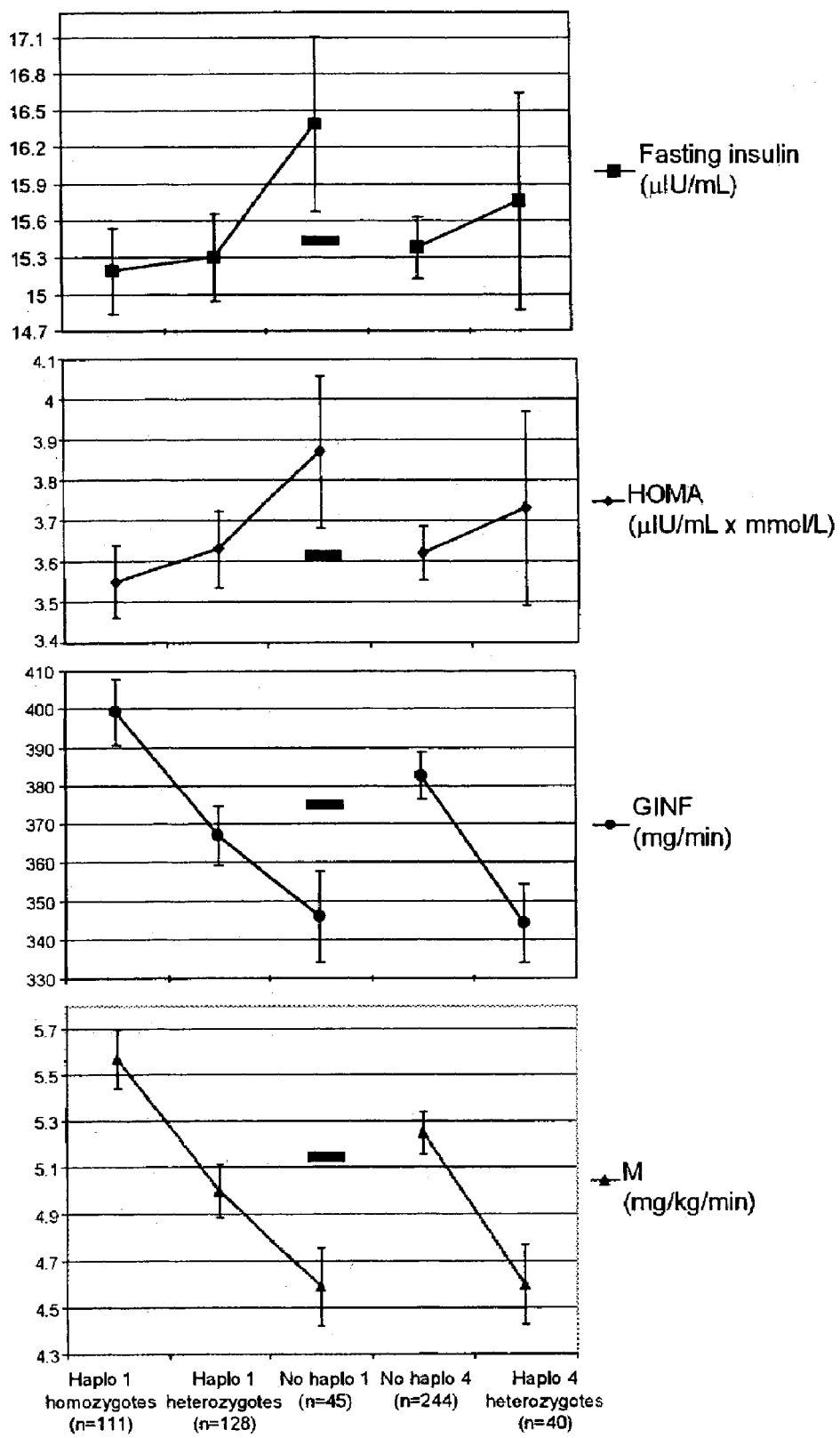
FIG. 2 shows the effect of LPL 3' end haplotypes on indices of insulin sensitivity. The thick line in the center of each graph represents the mean for the entire haplotyped and clamped population.
Figure 3:
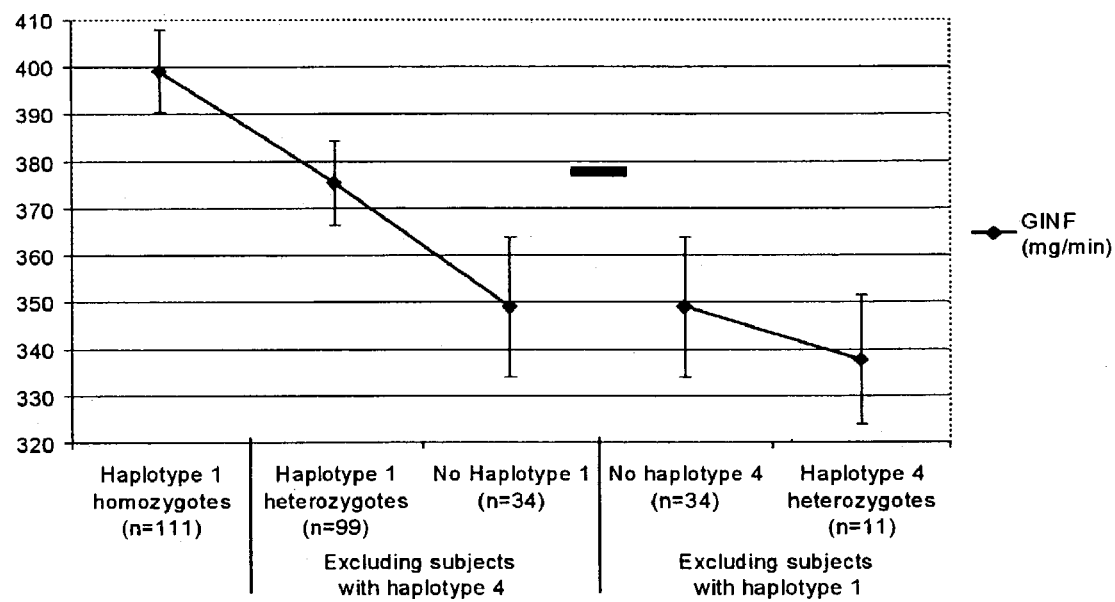
FIG. 3 shows independent effects of haplotype 1 and haplotype 4 on insulin sensitivity. On the left are haplotype 1 genotypes with haplotype 4 carriers removed. On the right are haplotype 4 genotypes with haplotype 1 carriers removed. The thick line in between represents the mean GINF level for the entire haplotyped and clamped population.

Association was evaluated by quantitative transmission disequilibrium testing. Positive association results for particular haplotypes are shown in Table 12 (below). No haplotype was significantly associated with fasting glucose, fasting insulin, or HOMA, but both haplotypes 1 and 4 were significantly associated with both GINF and the M value. To characterize the nature of the associations of haplotypes 1 and 4 with insulin resistance, we determined the mean levels of insulin sensitivity in carriers of these haplotypes (Table 12 and FIG. 2). We observed that haplotype I is associated with the most favorable mean insulin sensitivity, while carriers of haplotype 4 had the lowest insulin sensitivity (i.e. the greatest insulin resistance). For fasting insulin, HOMA, GINF, and M, mean insulin sensitivity progressively worsened going from haplotype 1 homozygotes to haplotype 1 heterozygotes to individuals without haplotype 1. Conversely, haplotype 4 heterozygotes were more insulin resistant than those without haplotype 4 (no haplotype 4 homozygotes were observed among the clamped subjects). FIG. 3 further explores these associations by examining the effects of haplotypes 1 and 4 on insulin sensitivity independently. Exclusion of subjects with haplotype 4 from haplotype I heterozygotes and those without haplotype 1 did not affect the trend of benefit on insulin sensitivity seen with increasing numbers of haplotype 1. Similarly, excluding haplotype 1 carriers from those with and without haplotype 4 did not affect the trend of lower insulin sensitivity in the latter subjects; in fact, the subjects without haplotype 1 who were carriers of haplotype 4 had the lowest insulin sensitivity (most insulin resistance) compared to the other haplogenotype groups. Similar trends were observed with M value.

TABLE 12

LPL haplotype association results for indices of insulin sensitivity.

| Phenotype | Haplotype | P value for association (from QTDT) | Mean trait value for haplotype carriers |
|---|---|---|---|
| GINF | 1 | 0.031 | 383.0 mg/min |
|  | 4 | 0.007 | 344.3 mg/min |
| M | 1 | 0.031 | 5.3 mg/kg/min |
|  | 4 | 0.005 | 4.6 mg/kg/min |

It is believed that the study described hereinabove is the first that has used insulin sensitivity assessed by the euglycemic clamp as the phenotype in an association study with LPL. Two LPL haplotypes were associated with variation in GINF. These haplotypes had opposite effects on insulin sensitivity. Haplotype 1, the most common haplotype, was associated with improved insulin sensitivity. As the number of chromosomes in an individual with haplotype 1 decreased (from two, to one, to none), insulin sensitivity by GINF, as well as HOMA and fasting insulin, decreased progressively. Furthermore, haplotype 4 carriers had the lowest insulin sensitivity, i.e. they were the most insulin resistant. The direction of these associations persisted when the haplotypes were considered separately. With the available data we cannot determine whether there is an insulin-sensitizing functional variant on haplotype 1 chromosomes and/or a variant on haplotype 4-bearing chromosomes that promotes insulin resistance. However, in terms of the relation to cardiovascular risk associated with the metabolic syndrome, our previous work has shown that haplotype 1 is associated with protection against coronary artery disease and haplotype 4 may be associated with increased risk of coronary artery disease (see Example 1 hereinabove).

REFERENCES CITED

1. Wu, D. A., Bu, X., Warden, C. H., Shen, D. D., Jeng, C. Y., Sheu, W. H., Fuh, M. M., Katsuya, T., Dzau, V. J., Reaven, G. M. et al. (1996) Quantitative trait locus mapping of human blood pressure to a genetic region at or near the lipoprotein lipase gene locus on chromosome 8p22. J. Clin. Invest., 97, 2111–2118.
2. Ahn, Y. I., Ferrell, R. E., Hamman, R. F., and Kamboh, M. I. (1993) Association of lipoprotein lipase gene variation with the physiological components of the insulin-resistance syndrome in the population of the San Luis Valley, Colorado. Diabetes Care, 16, 1502–1506.
3. Lee, W. J., Sheu, W. H., Jeng, C. Y., Young, M. S., and Chen, Y. T. (2000) Associations between lipoprotein lipase gene polymorphisms and insulin resistance in coronary heart disease. Chung-Hua I Hsueh Tsa Chih [Chinese Medical Journal], 63, 563–572.
4. Humphries, S. E., Nicaud, V., Margalef, J., Tiret, L., and Talmud, P. J. (1998) Lipoprotein lipase gene variation is associated with a paternal history of premature coronary artery disease and fasting and postprandial plasma triglycerides: the European Atherosclerosis Research Study (EARS). Arterioscler. Thromb. Vasc. Biol., 18, 526–534.
5. Templeton, A. R., Clark, A. G., Weiss, K. M., Nickerson, D. A., Boerwinkle, E, and Sing, C. F. (2000) Recombinational and mutational hotspots within the human lipoprotein lipase gene. Am. J. Hum. Genet., 66, 69–83.
6. Templeton, A. R., Weiss, K. M., Nickerson, D. A., Boerwinkle, E., and Sing, C. F. (2000) Cladistic structure within the human lipoprotein lipase gene and its implications for phenotypic association studies. Genetics, 156, 1259–1275.
7. Clark, A. G., Weiss, K. M., Nickerson, D. A., Taylor, S. L., Buchanan, A., Stengard, J., Salomaa, V., Vartiainen, E., Perola, M., Boerwinkle, E. et al. (1998) Haplotype structure and population genetic inferences from nucleotide-sequence variation in human lipoprotein lipase. Am. J. Hum. Genet., 63, 595–612.
8. Nicklas, B. J., Ferrell, R. E., Rogus, E. M., Berman, D. M., Ryan, A. S., Dennis, K. E., and Goldberg, A. P. (2000) Lipoprotein lipase gene variation is associated with adipose tissue lipoprotein lipase activity, and lipoprotein lipid and glucose concentrations in overweight postmenopausal women. Hum. Genet., 106, 420–424.
9. Nickerson, D. A., Taylor, S. L., Weiss, K. M., Clark, A. G., Hutchinson, R. G., Stengard, J., Salomaa, V., Vartiainen, E., Boerwinkle, E., and Sing, C. F. (1998) DNA sequence diversity in a 9.7-kb region of the human lipoprotein lipase gene. Nat. Genet., 19, 233–240.
10. Livak, K. J. (1999) Allelic discrimination using fluorogenic probes and the 5' nuclease assay. Genet. Anal., 14, 143–149.
11. Sobel, E. and Lange, K. (1996) Descent graphs in pedigree analysis: applications to haplotyping, location scores, and marker-sharing statistics. Am. J. Hum. Genet., 58, 1323–1337.
12. Felsenstein, J. (T989) PHYLIP—phylogeny inference package (version 3.2). Cladistics, 5, 164–166.
13. Daly M J, Rioux J D, Schaffner S F, Hudson T J, Lander E S. High-resolution haplotype structure in the human genome. Nat Genet 2001;29:229–232.
14. Rioux J D, Daly M J, Silverberg M S, Lindblad K, Steinhart H, Cohen Z, Delmonte T, Kocher K, Miller K, Guschwan S, Kulbokas E J, O'Leary S, Winchester E, Dewar K, Green T, Stone V, Chow C, Cohen A, Langelier D, Lapointe G, Gaudet D, Faith J, Branco N, Bull S B, McLeod R S, Griffiths A M, Bitton A, Greenberg G R, Lander E S, Siminovitch K A, Hudson T J. Genetic variation in the 5q31 cytokine gene cluster confers susceptibility to Crohn disease. Nat Genet 2001;29:223–228.
15. Gabriel S B, Schaffner S F, Nguyen H, Moore J M, Roy J, Blumenstiel B, Higgins J, DeFelice M, Lochner A, Faggart M, Liu-Cordero S N, Rotimi C, Adeyemo A, Cooper R, Ward R, Lander E S, Daly M J, Altshuler D. The structure of haplotype blocks in the human genome. Science 2002;296:2225–2229.
16. Templeton A R, Sing C F, Kessling A, Humphries S. A cladistic analysis of phenotype associations with haplotypes inferred from restriction endonuclease mapping. II. The analysis of natural populations. Genetics 1988;120: 1145–1154.
17. Templeton A R. Cladistic approaches to identifying determinants of variability in multifactorial phenotypes and the evolutionary significance of variation in the human genome. Ciba Found Symp 1996;197:259–277.
18. Murthy V, Julien P, Gagne C. Molecular pathobiology of the human lipoprotein lipase gene. Pharmacol Ther 1996; 70: 101–135.
19. Sobel E, Lange K. Descent-graphs in pedigree analysis: applications to haplotyping, location scores, and marker-sharing statistics. Am J Hum Genet 1996;58:1323–1337.
20. SAS [computer program]. Release 8.0. Cary, N C: SAS Institute, 1999.
21. Motulsky A G, Brunzell J D. Genetics of coronary atherosclerosis. In: King R A, Rotter J I, Motulsky A G, eds. The Genetic Basis of Common Diseases. New York, N.Y.: Oxford University Press, Inc., 2002:105–126.
22. Park Y W, Zhu S, Palaniappan L, Heshka S, Carnethon M R, Heymsfield S B. The metabolic syndrome: prevalence and associated risk factor findings in the US population from the Third National Health and Nutrition Examination Survey, 1988–1994. Arch Intern Med 2003; 163:427–36.
23. Pyorala M, Miettinen H, Laakso M, Pyorala K. Hyperinsulinemia predicts coronary heart disease risk in healthy middle-aged men: the 22-year follow-up results of the Helsinki Policemen Study. Circulation 1998;98:398–404.
24. Hanley A J, Williams K, Stern M P, Haffner S M. Homeostasis model assessment of insulin resistance in relation to the incidence of cardiovascular disease: the San Antonio Heart Study. Diabetes Care 2002;25:1177–84.
25. Allayee H, de Bruin T W, Michelle Dominguez K, et al. Genome scan for blood pressure in Dutch dyslipidemic families reveals linkage to a locus on chromosome 4p. Hypertension 2001;38:773–8.
26. Holmer S R, Hengstenberg C, Mayer B, et al. Lipoprotein lipase gene polymorphism, cholesterol subfractions and myocardial infarction in large samples of the general population. Cardiovascular Research 2000;47:806–12.
27. Heizmann C, Kirchgessner T, Kwiterovich P O, et al: DNA polymorphism haplotypes of the human lipoprotein lipase gene: possible association with high density lipoprotein levels. Hum Genet 1991;86:578–84.
28. Jemaa R, Tuzet S, Portos C, Betoulle D, Apfelbaum M, Fumeron F. Lipoprotein lipase gene polymorphisms: associations with hypertriglyceridemia and body mass index in obese people. Int J Obes Relat Metab Disord 1995;19:270–4.
29. Mattu R K, Needham E W, Morgan R, et al. DNA variants at the LPL gene locus associate with angiographically defined severity of atherosclerosis and serum lipoprotein levels in a Welsh population. Arterioscler Thromb 1994;14:1090–7.
30. Goodarzi M O, Guo X, Taylor K D, et al. Determination and use of haplotypes: ethnic comparison and association of the lipoprotein lipase gene and coronary artery disease in Mexican-Americans. Genet Med 2003;5.
31. Preiss-Landl K, Zimmermann R, Hammerle G, Zechner R. Lipoprotein lipase: the regulation of tissue specific expression and its role in lipid and energy metabolism. Curr Opin Lipidol 2002;13:471–81.

32. Mead J R, Ramji D P. The pivotal role of lipoprotein lipase in atherosclerosis. Cardiovasc Res 2002;55:261–9.
33. Proenza A M, Poissonnet C M, Ozata M, et al. Association of sets of alleles of genes encoding beta3-adrenoreceptor, uncoupling protein 1 and lipoprotein lipase with increased risk of metabolic complications in obesity. Int J Obes Relat Metab Disord 2000;24:93–100.
34. Cole S A, Aston C E, Hamman R F, Ferrell R E. Association of a PvuII RFLP at the lipoprotein lipase locus with fasting insulin levels in Hispanic men. Genet Epidemiol 1993;10: 177–88.
35. Ahn Y I, Kamboh M I, Hamman R F, Cole S A, Ferrell R E. Two DNA polymorphisms in the lipoprotein lipase gene and their associations with factors related to cardiovascular disease. J Lipid Res 1993;34:421–8.
36. Samuels M E, Forbey K C, Reid J E, et al. Identification of a common variant in the lipoprotein lipase gene in a large Utah kindred ascertained for coronary heart disease: the 93G/D9N variant predisposes to low HDL-C/high triglycerides. Clin Genet 2001;59:88–98.
37. Ukkola O, Garenc C, Perusse L, et al. Genetic variation at the lipoprotein lipase locus and plasma lipoprotein and insulin levels in the Quebec Family Study. Atherosclerosis 2001;158:199–206.
38. DeFronzo R A, Tobin J D, Andres R. Glucose clamp technique: a method for quantifying insulin secretion and resistance. Am J Physiol 1979;237: E214–23.
39. Wallace T M, Matthews D R. The assessment of insulin resistance in man. Diabet Med 2002;19:527–34.
40. O'Connell J R, Weeks D E. PedCheck: a program for identification of genotype incompatibilities in linkage analysis. Am J Hum Genet 1998;63:259–66.
41. Matthews D R, Hosker J P, Rudenski A S, Naylor B A, Treacher D F, Turner R C. Homeostasis model assessment: insulin resistance and beta-cell function from fasting plasma glucose and insulin concentrations in man. Diabetologia 1985;28:412–9.
42. Haseman J K, Elston R C. The investigation of linkage between a quantitative trait and a marker locus. Behav Genet 1972;2:3–19.
43. S.A.G.E.: Statistical Analysis for Genetic Epidemiology [computer program]. Cork, Ireland: Statistical Solutions, Ltd., 2002.
44. Elston R C, Buxbaum S, Jacobs K B, Olson J M. Haseman and Elston revisited. Genet Epidemiol 2000; 19:1–17.
45. Abecasis G R, Cardon L R, Cookson W O. A general test of association for quantitative traits in nuclear families. Am J Hum Genet 2000;66:279–92.
46. Spielman R S, McGinnis R E, Ewens W J. Transmission test for linkage disequilibrium: the insulin gene region and insulin-dependent diabetes mellitus (IDDM). Am J Hum Genet 1993;52:506–16.
47. Allison D B. Transmission-disequilibrium tests for quantitative traits. Am J Hum Genet 1997;60:676–90.
48. Abecasis G R, Cookson W O, Cardon L R. Pedigree tests of transmission disequilibrium. Eur J Hum Genet 2000; 8:545–51.
49. Okosun I S, Liao Y, Rotimi C N, Prewitt T E, Cooper R S. Abdominal adiposity and clustering of multiple metabolic syndrome in White, Black and Hispanic Americans. Ann Epidemiol 2000;10:263–70.
50. Haffner S M, Stern M P, Hazuda H P, Pugh J, Patterson J K, Malina R. Upper body and centralized adiposity in Mexican Americans and non-Hispanic whites: relationship to body mass index and other behavioral and demographic variables. Int J Obes 1986;10:493–502.
51. Despres J P, Lamarche B, Mauriege P, et al. Hyperinsulinemia as an independent risk factor for ischemic heart disease. N Engl J Med 1996;334:952–7.
52. Freeman M S, Mansfield M W, Barrett J H, Grant P J. Heritability of features of the insulin resistance syndrome in a community-based study of healthy families. Diabet Med 2002;19:994–9.
53. Hong Y, Pedersen N L, Brismar K, de Faire U. Genetic and environmental architecture of the features of the insulin-resistance syndrome. Am J Hum Genet 1997; 60:143–52.
54. Mitchell B D, Kammerer C M, Mahaney M C, et al. Genetic analysis of the IRS. Pleiotropic effects of genes influencing insulin levels on lipoprotein and obesity measures. Arterioscler Thromb Vasc Biol 1996; 16:281–8.
55. Boden G, Lebed B, Schatz M, Homko C, Lemieux S. Effects of acute changes of plasma free fatty acids on intramyocellular fat content and insulin resistance in healthy subjects. Diabetes 2001;50:1612–7.
56. Phillips D I, Caddy S, Ilic V, et al. Intramuscular triglyceride and muscle insulin sensitivity: evidence for a relationship in nondiabetic subjects. Metabolism 1996; 45:947–950.
57. Guerre-Millo M. Adipose tissue hormones. J Endocrinol Invest 2002; 25:855–61.
58. Malloy M J, Kane J P. A risk factor for atherosclerosis: triglyceride-rich lipoproteins. Adv Intern Med 2001; 47:111–36.
59. Gaziano J M, Hennekens C H, O'Donnell C J, Breslow J L, Buring J E. Fasting triglycerides, high-density lipoprotein, and risk of myocardial infarction. Circulation 1997; 96:2520–5.
60. Eisenberg S. High density lipoprotein metabolism. J Lipid Res 1984; 25:1017–58.
61. Bergman R N, Zaccaro D J, Watanabe R M, et al. Minimal model-based insulin sensitivity has greater heritability and distinct genetic basis than HOMA or fasting insulin. Diabetes 2003; In press.

We claim:

1. A method of detecting a genetic predisposition in a Mexican-American human subject for developing insulin resistance, comprising:
   a) collecting a biological sample from the subject;
   b) genotyping the sample at nucleotide positions 7315, 8292, 8393, 8852, 9040, and 9712 SEQ ID NO: 25; and
   c) assessing whether a haplotype is present in the sample, the haplotype comprising (nucleotide position: variant allele):
   (i) 7315: G;
   (ii) 8292: A;
   (iii) 8393: G;
   (iv) 8852: G;
   (v) 9040: G; and
   (vi) 9712: G, wherein the presence of the haplotype indicates a genetic predisposition for developing insulin resistance in the subject.

2. A method of detecting a lower than normal risk in a Mexican-American human subject for developing insulin resistance, comprising:
   a) collecting a biological sample from the subject;
   b) genotyping the sample at nucleotide positions 7315, 8292, 8393, 8852, 9040 SEQ ID NO: 25; and c) assessing whether a haplotype is present in the sample, the haplotype comprising (nucleotide position:variant allele):
  (i) 7315: G;
  (ii) 8292: A;
  (iii) 8393: T;
  (iv) 8852: T;
  (v) 9040: C; and
  (vi) 9712: G,
wherein the presence of the haplotype indicates a lower than normal risk for developing insulin resistance in the subject.

3. A method of detecting a lower than normal risk in a Mexican-American human subject for developing coronary artery disease, comprising:
  a) collecting a biological sample from the subject;
  b) genotyping the sample at nucleotide positions 7315, 8292, 8393, 8852, 9040 SEQ ID NO: 25; and
  c) assessing whether the sample is homozygous for a haplotype comprising (nucleotide position: variant allele):
    (i) 7315: G;
    (ii) 8292: A;
    (iii) 8393: T;
    (iv) 8852: T;
    (v) 9040: C; and
    (vi) 9712: G,
wherein homozygosity for the haplotype indicates a lower than normal risk for developing coronary artery disease in the subject.

* * * * *

UNITED STATES PATENT AND TRADEMARK OFFICE
CERTIFICATE OF CORRECTION

PATENT NO. : 7,141,373 B2 Page 1 of 1
APPLICATION NO. : 10/463301
DATED : November 28, 2006
INVENTOR(S) : Kent D. Taylor et al.

It is certified that error appears in the above-identified patent and that said Letters Patent is hereby corrected as shown below:

Column 49, line 60, insert --of-- between "9712" and "SEQ ID NO: 25;"

Column 50, line 67, insert --and 9712 of-- between "9040" and "SEQ ID NO: 25;"

Column 51, line 17, insert --and 9712 of-- between "9040" and "SEQ ID NO: 25;"

Signed and Sealed this

Tenth Day of April, 2007

JON W. DUDAS
*Director of the United States Patent and Trademark Office*